(12) United States Patent
Coates et al.

(10) Patent No.: US 9,376,413 B1
(45) Date of Patent: *Jun. 28, 2016

(54) SUCCINIC ANHYDRIDES FROM EPOXIDES

(71) Applicant: Cornell University, Ithaca, NY (US)

(72) Inventors: Geoffrey W. Coates, Lansing, NY (US); John M. Rowley, Houghton, NY (US)

(73) Assignee: Cornell University, Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/552,825

(22) Filed: Nov. 25, 2014

Related U.S. Application Data

(63) Continuation of application No. 13/914,592, filed on Jun. 10, 2013, now Pat. No. 8,921,581, which is a continuation of application No. 12/204,411, filed on Sep. 4, 2008, now Pat. No. 8,481,756.

(60) Provisional application No. 61/040,944, filed on Mar. 31, 2008, provisional application No. 60/935,845, filed on Sep. 4, 2007.

(51) Int. Cl.
   *C07D 307/60* (2006.01)
(52) U.S. Cl.
   CPC .................... *C07D 307/60* (2013.01)
(58) Field of Classification Search
   CPC .................................................. C07D 307/60
   USPC ....................................................... 549/233
   See application file for complete search history.

(56) References Cited

U.S. PATENT DOCUMENTS

| | | |
|---|---|---|
| 6,133,402 A | 10/2000 | Coates et al. |
| 6,852,865 B2 | 2/2005 | Coates et al. |
| 7,304,172 B2 | 12/2007 | Coates et al. |
| 7,569,709 B2 | 8/2009 | Coates et al. |
| 8,481,756 B1 | 7/2013 | Coates et al. |
| 8,921,581 B1 | 12/2014 | Coates et al. |
| 2003/0162961 A1 | 8/2003 | Coates et al. |
| 2006/0089252 A1 | 4/2006 | Coates et al. |
| 2007/0213524 A1 | 9/2007 | Coates et al. |
| 2007/0255039 A1 | 11/2007 | Coates et al. |
| 2008/0108499 A1 | 5/2008 | Coates et al. |
| 2009/0287000 A1 | 11/2009 | Coates et al. |

OTHER PUBLICATIONS

Getzler, Y.D.Y.L et al., Catalytic Carbonylation of β-Lactones to Succinic Anhydrides, Journal of the American Chemical Society, 126:6842-6843 (2004).
Rowley, J.M. et al., Catalytic Double Carbonylation of Epoxides to Succinic Anhydrides: Catalyst Discover, Reaction Scope, and Mechanism, Journal of the American Chemical Society, 129:4948-4960 (2007).

*Primary Examiner* — T. Victor Oh
(74) *Attorney, Agent, or Firm* — Choate, Hall & Stewart—LLP; Charles E. Lyon; Danielle M. Nihan

(57) ABSTRACT

Catalysts and methods for the double carbonylation of epoxides are disclosed. Each epoxide molecule reacts with two molecules of carbon monoxide to produce a succinic anhydride. The reaction is facilitated by catalysts combining a Lewis acidic species with a transition metal carbonyl complex. The double carbonylation is achieved in single process by using reaction conditions under which both carbonylation reactions occur without the necessity of isolating or purifying the product of the first carbonylation.

27 Claims, 4 Drawing Sheets

US 9,376,413 B1

SUCCINIC ANHYDRIDES FROM EPOXIDES

PRIORITY INFORMATION

The present application claims priority to U.S. Provisional No. 60/935,845 filed Sep. 4, 2007 and U.S. Provisional No. 61/040,944 filed Mar. 31, 2008. The entire contents of these priority applications are incorporated herein by reference in their entirety.

GOVERNMENT SUPPORT

This invention was made with Government support under Grant No. NSF 0243605, awarded by the National Science Foundation and/or Grant No. DOE DE-FG02-05ER15687, awarded by the Department of Energy. The government has certain rights in the invention.

BACKGROUND

Succinic anhydrides are valuable reactive intermediates that find use in an array of applications.

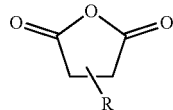

For example, their copolymerization with epoxides or diols yields biodegradable polyesters. Anhydrides are also useful intermediates in organic synthesis, since they can be readily ring opened to diacids or other succinate derivatives; some examples of which include biologically active natural products, pharmaceuticals, and metalloprotease inhibitors.

Substituted succinic anhydrides have previously been synthesized by a number of methods, most often by the dehydration of the corresponding diacid or from maleic anhydride via Diels-Alder or Ene reactions. They have also been made by metal catalyzed carbonylation of alkynes, alkenoic acids, and lactones; however, most of these catalytic reactions proceeded either in low yield, with significant side products, or without demonstrating substrate generality or product stereochemical purity. Thus, the development of more efficient and stereoselective syntheses remains an important goal.

As disclosed in U.S. Pat. No. 6,852,865 our group has developed a class of well-defined bimetallic catalysts of the general type [Lewis acid]$^+$[M(CO)$_x$]$^-$ for the ring-expanding carbonylation of strained heterocycles. We have found that related catalysts can carbonylate β-lactones to succinic anhydrides in high yields while preserving stereochemical purity. Given the many syntheses of enantiomerically pure epoxides and the recent advances in epoxide carbonylation to β-lactones, subsequent carbonylation of these lactones constitutes a versatile two-step method for the stereoselective synthesis of succinic anhydrides (Scheme 1).

Scheme 1

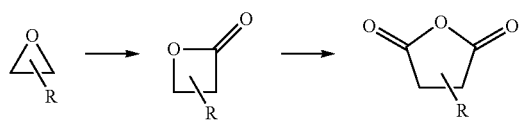

This method would be far more synthetically useful if the two steps could be consolidated, eliminating the requirement for isolation and purification of potentially toxic lactone intermediates, saving time and catalyst, and increasing overall yield. The present invention provides such a methodology.

SUMMARY

The double carbonylation of epoxides whereby each epoxide molecule reacts with two molecules of carbon monoxide to produce a succinic anhydride is facilitated by the catalysts and conditions of the present invention. The double carbonylation is achieved in a single process using reaction conditions under which both carbonylation reactions can occur without the necessity of isolating or purifying the product of the first carbonylation.

Scheme 2

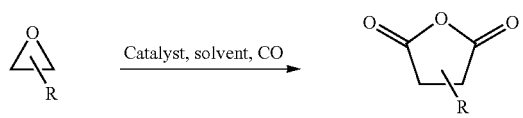

Using known catalysts and conditions, a useful process according to Scheme 2 has previously been unachievable since the two steps (lactone formation from an epoxide and anhydride formation from a lactone) were found to have different and often mutually exclusive reaction requirements. One aspect of the present invention encompasses catalyst/solvent combinations that enable this process to succeed in a single pot reaction format.

DETAILED DESCRIPTION OF CERTAIN EMBODIMENTS

Figure 1:
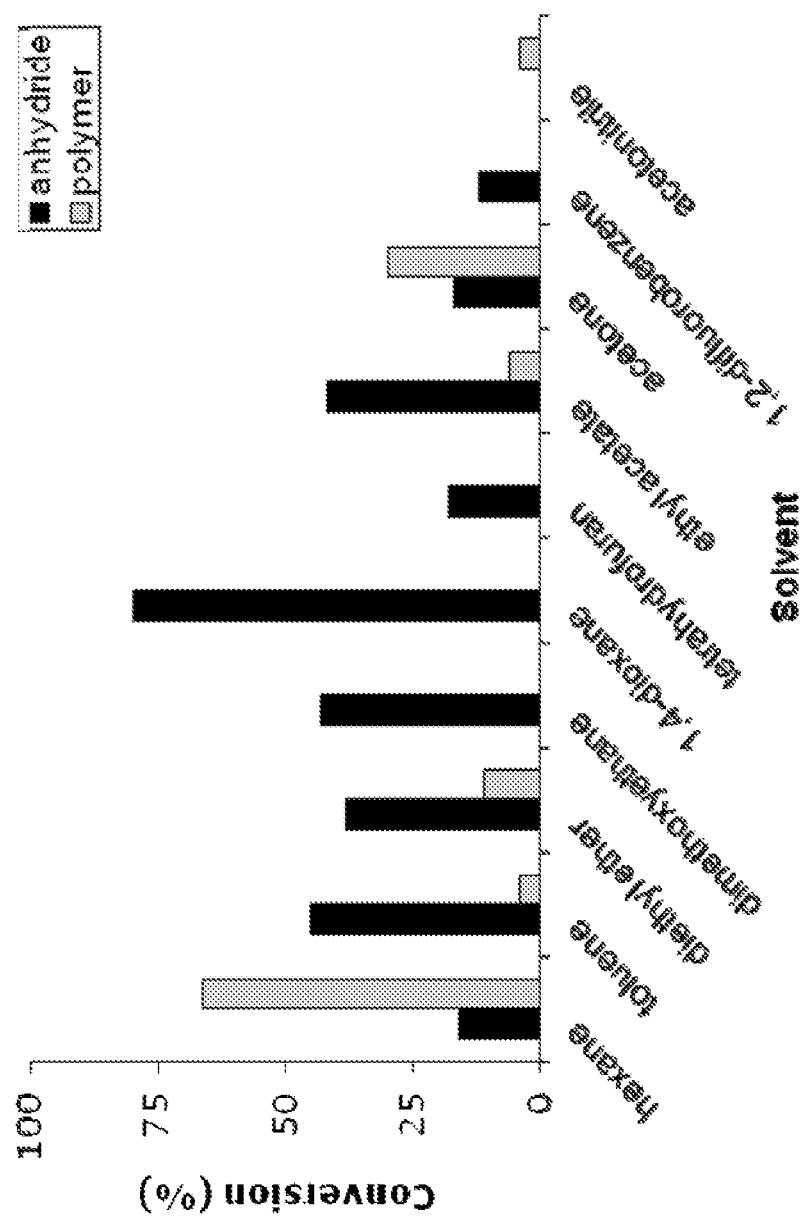
FIG. 1 illustrates the results of double carbonylation experiments using catalyst 1c in different solvents. Reaction conditions: 2 mmol epoxide in 1 mL solvent, 0.2 mol % catalyst 1c, 850 psi CO, 2 h, 90° C. Product distribution determined by $^1$H NMR spectrum of crude reaction mixture. Epoxide was completely converted to lactone (not shown) in all of these solvents; subsequent conversion of lactone to anhydride (black) and polymer (gray) is shown.

The present invention provides catalysts and methods that enable the double carbonylation of epoxides to provide succinic anhydride products. In general, the double carbonylation is performed in a solvent which includes a Lewis base. In certain embodiments, the Lewis base can be the epoxide (i.e., the reaction is performed in neat epoxide). In certain embodiments, the Lewis base is distinct from the epoxide. While methods that produce high crude yields of succinic anhydride are most useful (e.g., at least 50%, at least 70%, at least 80%, at least 90%, at least 95%, etc.), the present invention also encompasses methods that generate lower crude yields (e.g., at least 10%, at least 20%, etc.).

Epoxides

The methods are generally applicable and a wide range of epoxide starting materials can be used. The epoxide substrates (and by extension the lactone intermediates and anhydride products) may be unsubstituted (i.e., ethylene oxide) or may be monosubstituted, vicinally disubstituted (either cis or trans). The methods can also be applied to geminally disubstituted, trisubstituted or tetrasubstituted epoxides though these substrates react more slowly and tend to give lower yields of anhydride. The substituent(s) on the epoxide can be any that is compatible with the reaction conditions described herein.

In certain embodiments, the epoxide has the formula I:

The R group and any other chemical variable appearing in the Schemes and structures described herein encompass those chemical moieties and functional groups that would be recognized by one having skill in the art of organic chemistry as being compatible with the structure and function of the molecules bearing those chemical variables. Exemplary functional groups include substituted and unsubstituted cyclic and acyclic hydrocarbon moieties, substituted and unsubstituted cyclic and acyclic heteroatom-containing moieties, as well as common functional groups comprising heteroatoms, halogens, and metalloid elements. To further define the range of suitable groups certain definitions are provided below. Nonetheless, it is to be understood that these definitions are meant to be representative and the absence of a specific group or moiety in the definitions below is not necessarily meant to exclude such groups or to imply that such a group is not encompassed by the present invention.

In any case where a chemical variable is shown attached to a bond that crosses a bond of ring (for example as shown for R above, $R^d$ in certain ligands below, etc.), this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

In one embodiment of the epoxides of formula I, each R group can be independently selected from the group consisting of: (a) $C_1$ to $C_{20}$ alkyl; (b) $C_2$ to $C_{20}$ alkenyl; (c) $C_2$ to $C_{20}$ alkynyl; (d) up to a $C_{12}$ carbocycle; (e) up to a $C_{12}$ heterocycle; (f) —$C(R^{13})_zH_{(3-z)}$; and (g) a polymer chain. Two or more R groups may be taken together with the carbon atoms to which they are attached to form one or more rings, and any of (a) through (e) may optionally be further substituted with one or more F groups.

F at each occurrence can be independently selected from the group consisting of: halogen; —$OR^{10}$; —$OC(O)R^{13}$; —$OC(O)OR^{13}$; —$OC(O)NR^{11}R^{12}$; —CN; —CNO; —$C(O)R^{13}$; —$C(O)OR^{13}$; —$C(O)NR^{11}R^{12}$; —$C(R^{13})_zH_{(3-z)}$; —$NR^{11}C(O)R^{10}$; —$NR^{11}C(O)OR^{10}$; —NCO; —$NR^{12}SO_2R^{13}$; —$S(O)_xR^{13}$; —$S(O)_2NR^{11}R^{12}$; —$NO_2$; —$N_3$; —$(CH_2)_kR^{14}$; —$(CH_2)_k$-Z-$R^{16}$; and —$(CH_2)_k$-Z-$(CH_2)_m$-$R^{14}$.

$R^{10}$ at each occurrence can be independently selected from the group consisting of: —$C(R^{13})_zH_{(3-z)}$; $C_1$ to $C_{12}$ alkyl; $C_2$ to $C_{12}$ alkenyl; $C_2$ to $C_{12}$ alkynyl; up to a $C_{12}$ carbocycle; up to a $C_{12}$ heterocycle; —$S(O)_2R^{13}$; —$Si(R^{15})_3$; —H; and a hydroxyl protecting group.

$R^{11}$ and $R^{12}$ at each occurrence can be independently selected from the group consisting of: —H; $C_1$ to $C_{12}$ alkyl; $C_2$ to $C_{12}$ alkenyl; $C_2$ to $C_{12}$ alkynyl; and —$C(R^{13})_zH_{(3-z)}$. $R^{11}$ and $R^{12}$, when both present, can optionally be taken together with the atom to which they are attached to form a 3- to 10-membered ring.

$R^{13}$ at each occurrence can be independently selected from the group consisting of: —H; $C_1$ to $C_{12}$ alkyl; $C_2$ to $C_{12}$ alkenyl; $C_2$ to $C_{12}$ alkynyl; up to a $C_{12}$ carbocycle; and up to a $C_{12}$ heterocycle.

$R^{14}$ at each occurrence can be independently selected from the group consisting of: halogen; —$OR^{10}$; —$OC(O)R^{13}$; —$OC(O)OR^{13}$; —$OC(O)NR^{11}R^{12}$; —CN; —CNO; —$C(R^{13})_zH_{(3-z)}$; —$C(O)R^{13}$; —$C(O)OR^{13}$; —$C(O)NR^{11}R^{12}$; —$NR^{11}C(O)R^{13}$; —$NR^{11}C(O)OR^{10}$; —$NR^{11}SO_2R^{13}$; —NCO; —$N_3$; —$NO_2$; —$S(O)_xR^{13}$; —$SO_2NR^{11}R^{12}$; up to a $C_{12}$ heterocycle; and up to a $C_{12}$ carbocycle.

$R^{15}$ at each occurrence can be independently selected from the group consisting of: $C_1$ to $C_6$ alkyl; $C_2$ to $C_6$ alkenyl; $C_2$ to $C_6$ alkynyl; and up to $C_{12}$ substituted or unsubstituted carbocycle.

$R^{16}$ at each occurrence can be independently selected from the group consisting of: $C_1$ to $C_{12}$ alkyl; $C_2$ to $C_{12}$ alkenyl; $C_2$ to $C_{12}$ alkynyl; up to a $C_{12}$ heterocycle; up to a $C_{12}$ carbocycle; and —$C(R^{13})_zH_{(3-z)}$.

Z is a divalent linker and can be selected from the group consisting of: —$(CH=CH)_a$—; —$(CH\equiv CH)_a$—; —C(O)—; —$C(=NOR^{11})$—; —$C(=NNR^{11}R^{12})$—; —O—; —$N(R^{11})$—; —$N(C(O)R^{13})$—; —$S(O)_x$—; a polyether; and a polyamine.

a can be 1, 2, 3, or 4.

k can be an integer from 1 to 8 inclusive.

m can be an integer from 1 to 8 inclusive.

x can be 0, 1, or 2.

z can be 1, 2, or 3.

It is to be understood that the present invention encompasses the use of epoxides which comprise any combination of these variable definitions. For example, as discussed in Example 4 and Table 2 below, we have applied the methods to the following representative unsubstituted and monosubstituted epoxides: ethylene oxide (4), propylene oxide (6), 1,2-epoxybutane (8); 1,2-epoxyhexane (10); 1,2-epoxydodecane (12); cyclohexyl oxirane (14); n-butyl glycidyl ether (16); tert-butyldimethylsilyl glycidyl ether (18); benzyl glycidyl ether (20); 10,11-epoxyundecan-1-ol (22); 4,5-epoxypentyl butyrate (24); 5,6-epoxyhexanenitrile (26); N,N-dimethyl-10,11-undecylamide (28); 1,2-epoxy-5-hexene (30); 1,2-epoxy-7-octene (32); (2,3-epoxypropyl)benzene (34); styrene oxide (36); and 1,2,7,8-diepoxyoctane (38). Ethylene oxide (4) and propylene oxide (6) are of particular commercial interest.

As discussed in Example 4 and Table 3 below, we have also applied the methods to the following representative disubstituted epoxides: cis-2,3-epoxybutane (40); trans-2,3-epoxybutane (42); trans-3,4-epoxyhexane (44); and trans-2,3-epoxyoctane (46).

As discussed in Example 4 and Table 4 below, we have also applied the methods to the following representative enantiomeric epoxides: (R)-propylene oxide ((R)-6); (S)-1,2-epoxyhexane ((S)-10); and (R)-benzyl glycidyl ether ((R)-20).

These representative epoxides demonstrate that the methods are applicable to a range of substituted epoxide substrates including those containing ethers, alcohols, esters, amides, nitriles, silyl ethers, alkenes and aromatics. It is to be understood that these lists are not exhaustive, other functional groups can also be present, for example ketone and acetal substituted epoxides have been successfully employed.

Catalysts

The present invention encompasses the use of carbonylation catalysts comprising a Lewis acid in combination with a transition metal carbonyl complex. The term Lewis acid as used herein refers to any electrophilic species that is capable of accepting an electron pair and that is not a Brønsted-Lowry acid.

In certain embodiments, the catalyst comprises a complex of formula [Lewis acid]$^{u+}${[QT(CO)$_v$]$^{s-}$}$_t$ where Q is any ligand and need not be present; T is a transition metal; u is an integer from 1 to 6 inclusive; s is an integer from 1 to 4 inclusive; t is a number such that t multiplied by s equals u; and v is an integer from 1 to 9 inclusive. For example, in one embodiment u and s are both 1. In another embodiment u and s are both 2. In certain embodiments, v is an integer from 1 to 4 inclusive. In one embodiment, v is 4.

Lewis Acids

In certain embodiments, the Lewis acid portion of the catalyst includes an element from groups 3 through 14 of the periodic table or contains a lanthanide metal. Useful Lewis acids may either be neutral (e.g., compounds such as $AlCl_3$, $CrCl_2$, $CrCl_3$, $ZnCl_2$, $BF_3$, $BCl_3$, $Yb(OTf)_3$, $FeCl_2$, $FeCl_3$, $CoCl_2$, etc.) or cationic (for instance, metal complexes of the formula [M(L)$_b$]$^{c+}$ where M is a metal, each L is a ligand, b is an integer from 1 to 6 inclusive, and c is 1, 2, or 3, and where, if more than one L is present, each L may be the same or different). A broad array of metallo Lewis acids have been found applicable to the present invention. In certain embodiments, M is a transition metal, a group 13 or 14 metal, or a lanthanide. Transition metals and group 13 metals are of particular interest. For example, in certain embodiments, M is aluminum, chromium, indium or gallium. In some embodiments, M is aluminum or chromium.

Similarly, a range of ligands (L) can be present in the metallo Lewis acid component of the catalyst. In certain embodiments the ligand can be a dianionic tetradentate ligand.

Suitable ligands include, but are not limited to: porphyrin derivatives 1, salen derivatives 2, dibenzotetramethyltetraaza[14]annulene (tmtaa) derivatives 3, phthalocyaninate derivatives 4, and derivatives of the Trost ligand 5. In certain embodiments, porphyrin, salen and tmtaa derivatives are of particular utility. In some cases, a mixture of more than one Lewis acid component can be present in the catalyst. Exemplary definitions for the R groups appearing in structures 1 through 5 are more fully described below.

In certain embodiments, the metal complex includes a metal M and a ligand L of formula 1:

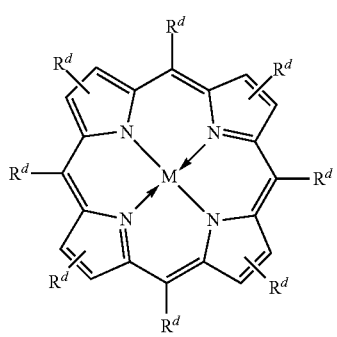

1 where R$^d$ at each occurrence is independently selected from the group consisting of: —H; C$_1$-C$_{12}$ alkyl; C$_2$-C$_{12}$ alkenyl; C$_2$-C$_{12}$ alkynyl; halogen; —OR$^{10}$; —OC(O)R$^{13}$; —OC(O)OR$^{13}$; —OC(O)NR$^{11}$R$^{12}$; —CN; —CNO; —C(O)R$^{13}$; —C(R$^{13}$)$_z$H$_{(3-z)}$; —C(O)OR$^{13}$; —C(O)NR$^{11}$R$^{12}$; —NR$^{11}$R$^{12}$; —NR$^{11}$C(O)R$^{10}$; —NR$^{11}$C(O)OR$^{13}$; —NR$^{11}$SO$_2$R$^{13}$; —NCO; —N$_3$; —NO$_2$; —S(O)$_x$R$^{13}$; —SO$_2$NR$^{11}$R$^{12}$; —C(R$^{13}$)$_z$H$_{(3-z)}$; —(CH$_2$)$_k$R$^{14}$; —(CH$_2$)$_k$-Z-R$^{16}$—; and —(CH$_2$)$_k$-Z-(CH$_2$)$_m$-R$^{14}$, and where R$^{10}$, R$^{11}$, R$^{12}$, R$^{13}$, R$^{14}$, R$^{16}$, Z, k, m, x, and z are as defined above.

In certain embodiments, the metal complex includes a metal M and a ligand L of formula 2:

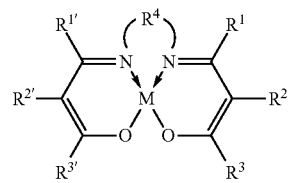

2 where R$^1$ and R$^{1'}$ are independently selected from the group consisting of: —H; C$_1$ to C$_{12}$ alkyl; C$_2$ to C$_{12}$ alkenyl; C$_2$ to C$_{12}$ alkynyl; —C(R$^{13}$)$_z$H$_{(3-z)}$; —(CH$_2$)$_k$R$^{14}$; and —(CH$_2$)$_k$-Z-R$^{14}$, where R$^2$, R$^{2'}$, R$^3$, and R$^{3'}$ are independently selected from the group consisting of: (i) C$_1$-C$_{12}$ alkyl; (ii) C$_2$-C$_{12}$ alkenyl; (iii) C$_2$-C$_{12}$ alkynyl; (iv) up to a C$_{12}$ carbocycle; (v) up to a C$_{12}$ heterocycle; (vi) —(CH$_2$)$_k$R$^{14}$; (vii) R$^{20}$; and (viii) —C(R$^{13}$)$_z$H$_{(3-z)}$, where each of (i) through (v) may optionally be further substituted with one or more R$^{20}$ groups; and where R$^2$ and R$^3$, and R$^{2'}$ and R$^{3'}$ may optionally be taken together with the carbon atoms to which they are attached to form one or more rings which may in turn be substituted with one or more R$^{20}$ groups; and where R$^4$ is selected from the group consisting of:

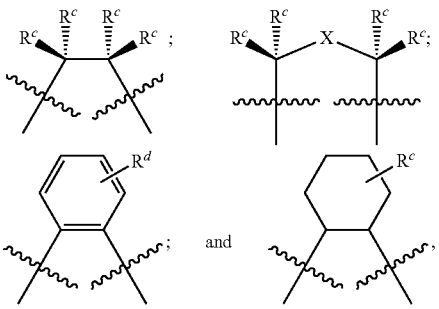

where X is a divalent linker selected from the group consisting of: —N(R$^{11}$)—; —O—; —S(O)$_x$—; —(CH$_2$)$_k$—; —C(O)—; —C(=NOR$^{10}$)—; —C(R$^c$)$_2$—; a polyether; a C$_3$ to C$_8$ substituted or unsubstituted carbocycle; and a C$_1$ to C$_8$ substituted or unsubstituted heterocycle, where R$^d$ is as defined above, where R$^c$ at each occurrence is independently selected from the group consisting of: (a) C$_1$-C$_{12}$ alkyl; (b) C$_2$-C$_{12}$ alkenyl, (c) C$_2$-C$_{12}$ alkynyl; (e) up to a C$_{12}$ carbocycle, (f) up to a C$_{12}$ heterocycle; (g) R$^{20}$; and (h) —C(R$^{13}$)$_z$H$_{(3-z)}$;

where two or more R$^c$ groups may be taken together with the carbon atoms to which they are attached to form one or more rings, where when two R$^c$ groups are attached to the same carbon atom, they may be taken together to form a moiety selected from the group consisting of: a 3- to 8-membered spirocyclic ring; a carbonyl (C=O), an oxime (C=NOR$^{10}$); a hydrazone (C=NNR$^{11}$R$^{12}$); an imine (C=NR$^{11}$); and an alkenyl group (C=CR$^{11}$R$^{12}$), and where any of (a) through (f) may optionally be further substituted with one or more R$^{20}$ groups, where R$^{20}$ at each occurrence is independently selected from the group consisting of: —H; halogen; —OR$^{10}$; —OC(O)R$^{13}$; 'OC(O)OR$^{13}$; —OC(O)NR$^{11}$R$^{12}$; —CN; —CNO; —C(O)R$^{13}$; —C(O)OR$^{13}$; —C(O)NR$^{11}$R$^{12}$; —C(R$^{13}$)$_z$H$_{(3-z)}$; —NR$^{11}$R$^{12}$; —NR$^{11}$C(O)R$^{10}$; —NR$^{11}$C(O)OR$^{10}$; —NCO; —NR$^{12}$SO$_2$R$^{13}$; —S(O)$_x$R$^{13}$; —S(O)$_2$NR$^{11}$R$^{12}$; —NO$_2$; —N$_3$; —(CH$_2$)$_k$R$^{14}$; —(CH$_2$)$_k$-Z-R$^{16}$; and —(CH$_2$)$_k$-Z-(CH$_2$)$_m$-R$^{14}$, and where R$^{10}$, R$^{11}$, R$^{12}$, R$^{13}$, R$^{14}$, R$^{16}$, Z, k, m, x, and z are as defined above.

In certain embodiments, the metal complex includes a metal M and a ligand L of formula 3:

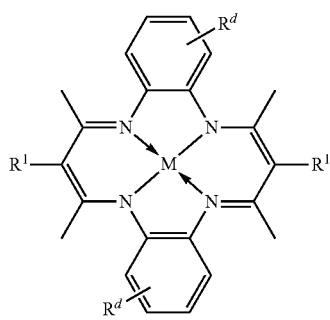

3 where R$^d$ is as defined above, where R$^1$ at each occurrence is independently selected from the group consisting of: —H; C$_1$ to C$_{12}$ alkyl; C$_2$ to C$_{12}$ alkenyl; C$_2$ to C$_{12}$ alkynyl; —C(R$^{13}$)$_z$H$_{(3-z)}$; —(CH$_2$)$_k$R$^{14}$; and —(CH$_2$)$_k$-Z-R$^{14}$, and where R$^{13}$, R$^{14}$, Z, k, and z are as defined above.

In certain embodiments, the metal complex includes a metal M and a ligand L of formula 4:

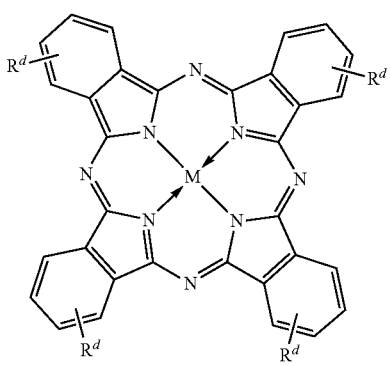

4 where R$^d$ is as defined above.

In certain embodiments, the metal complex includes a metal M and a ligand L of formula 5:

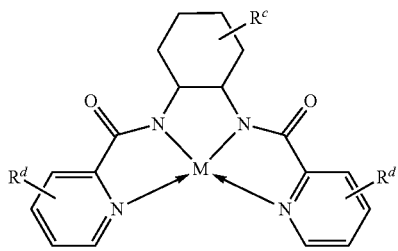

5 where R$^c$ and R$^d$ are as defined above.

Transition Metal Carbonyl Complexes

The transition metal carbonyl complex included in the catalyst may be neutral or anionic. In certain embodiments, the metal carbonyl complex is anionic, e.g., monoanionic carbonyl complexes of metals from groups 5, 7 or 9 of the periodic table or dianionic carbonyl complexes of metals from groups 4 or 8 of the periodic table. In certain embodiments, the metal carbonyl complex contains a metal from groups 7 or 9 of the periodic table, e.g., cobalt, manganese or rhodium. Examples of suitable anionic metal carbonyl complexes include, but are not limited to: [Co(CO)$_4$]$^-$ and [Mn(CO)$_5$]$^-$. In certain embodiments [Co(CO)$_4$]$^-$ may be used. In some cases, a mixture of two or more transition metal carbonyl complexes can be present in the catalyst.

While the metal carbonyl complexes disclosed herein are generally binary metal carbonyl complexes (i.e., they have the formula M(CO)$_y$ and consist only of a metal and carbonyl ligands) this is not a limiting requirement of the present invention, and the use of mixed ligand metal carbonyl complexes is also contemplated. For example, a bidentate phosphine ligand may be present along with the carbonyl ligands. It is also anticipated that under some reaction conditions, mixed ligand carbonyl complexes may be formed in situ from the binary complexes during the reaction. Whether added or formed in situ, catalysts containing mixed ligand carbonyl complexes are encompassed by the present invention.

The stoichiometry of the Lewis acid and the metal carbonyl complex components of the catalyst encompassed by the present invention can be varied. Typically, the two components are present in a ratio that balances the charges of the two species. For example, if the Lewis acid is a monocation and the metal carbonyl complex is a dianion, then they can be present in a charge-balancing ratio of 2:1 (i.e., 2 [Lewis acid]$^+$+[M(CO)$_x$]$^{2-}$). In some cases, if the charge of the carbonyl complex exceeds that of the Lewis acid component—either because there is a stoichiometric excess of the former, or because the Lewis acid is a neutral species—then the excess negative charge of the carbonyl complex can be balanced by the presence of a group 1 or 2 metal cation, or by a non-metallic cation such as an ammonium, phosphonium, or arsonium cation.

In some cases, the metal atom of the metallo Lewis acid can be coordinated to one or more additional neutral coordinating ligands (for instance to satisfy the metal atom's coordination valence) one such ligand that is particularly preferred is tetrahydrofuran (THF), it will be understood however that many other solvents and other ligands such as are well known in the art may also fulfill this role without departing from the present invention. It will also be realized that under reaction conditions, the coordinating ligands can be replaced by reagents, products, intermediates or solvents that may be present. Such in situ-generated species are also encompassed by the present invention. As with many catalytic processes, the structure of the specific catalyst added to the reaction will not always be the active species.

In a related vein, catalysts suitable for the processes of the present invention can be formed in situ from individual components. For example, the Lewis acid and the metal carbonyl complex can be added separately to the reaction vessel in which the reaction is performed. In one specific example of this, instead of adding aluminum tetrakis-(4-chlorophenyl)-porphine bis-tetrahydrofuran tetracarbonylcobaltate (1c) as the catalyst, one can separately add aluminum tetrakis-(4-chlorophenyl)-porphine chloride and sodium tetracarbonyl cobaltate. In a similar procedure, an aluminum porphyrin tetrafluoroborate compound (TPP(Al)$^+$BF$_4^-$) was combined in situ with bis(triphenylphosphine)iminium tetracarbonyl cobaltate (PPN$^+$Co(CO)$_4^-$) to provide the active catalyst. It is metal carbonyl complex can be present in an excess ranging from about 2-fold to about 10-fold. If there is an excess of an anionic metal carbonyl complex relative to the Lewis acid, then the negative charge can be balanced as described above, the excess negative charge is balanced by the presence of an alkali or alkaline earth metal.

Below we present the structures of some exemplary catalysts that can be used in methods of the present invention.

In certain embodiments, the catalyst comprises a complex of formula 1a, 1b, 1c, 1d, 1e or 1f:

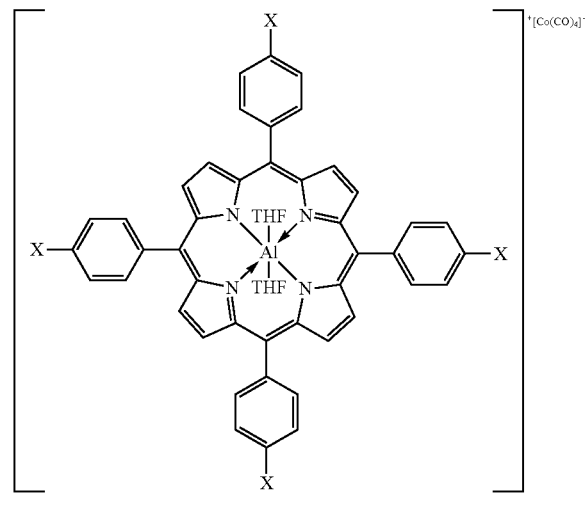

1a X = H
1b X = CH$_3$
1c X = Cl
1d X = F
1e X = CF$_3$
1f X = OCH$_3$ thus to be understood that such combinations of reagents that will produce a Lewis acid/metal carbonyl pair in situ are within the scope of the present invention.

Without wishing to be bound by any theory or to thereby limit the scope of the invention, it is believed that catalysts combining a Lewis acid component that is cationic and a metal carbonyl complex that is anionic are particularly suitable for carbonylation processes of the present invention. It is further believed that Lewis acid/metal carbonyl combinations that have a propensity to form non-ionic associations may be less effective (for instance if a covalent or coordinate covalent bond is prone to form between the metals of the two components). In such cases it can be advantageous to add additional components that prevent this association. As one example, when the Lewis acid component is based on an indium porphyrin complex, and the metal carbonyl component is tetracarbonyl cobaltate, the carbonylation reaction is improved by addition of triphenylphosphine. Again without being bound by theory or thereby limiting the scope of the present invention, the phosphine is believed to coordinate with the indium and thereby disrupt its propensity to bind to the cobaltate component of the catalyst.

In some cases, it has been found advantageous to have an excess of the transition metal carbonyl component of the catalyst present in the reaction mixture. For instance, the In certain embodiments, the catalyst comprises a complex of formula 1g:

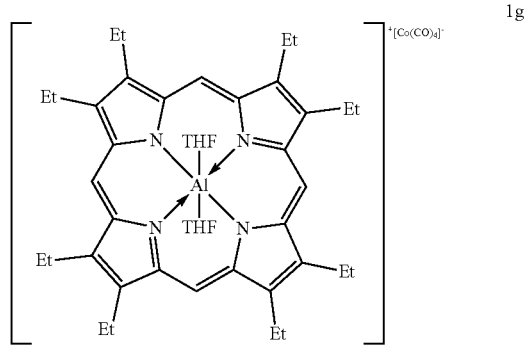

In certain embodiments, the catalyst comprises a complex of formula 1h:
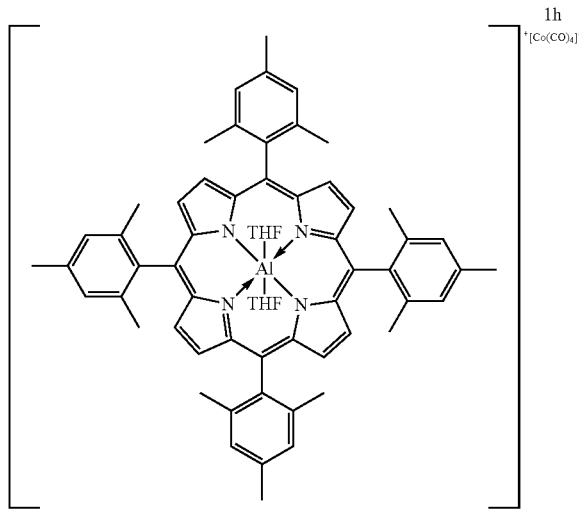
In certain embodiments, the catalyst comprises a complex of formula 1i, 1j, 1k, 1l, 1m or 1n:
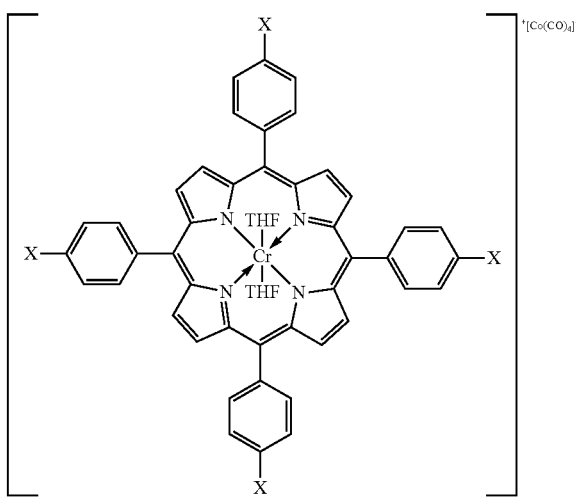
1i X = H
1j X = CH$_3$
1k X = Cl
1l X = F
1m X = CF$_3$
1n X = OCH$_3$ In certain embodiments, the catalyst comprises a complex of formula 1o:
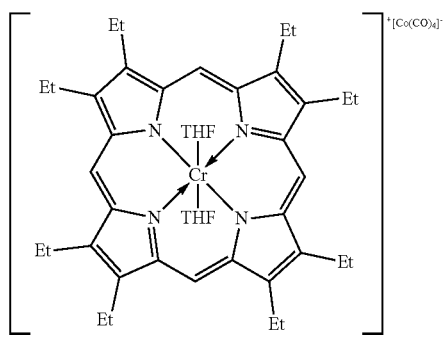
1o
In certain embodiments, the catalyst comprises a complex of formula 1p:
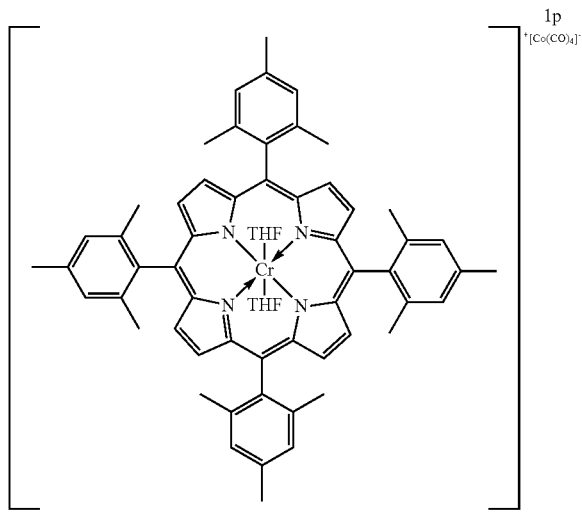
1p
In certain embodiments, the catalyst comprises a complex of formula 2a or 2b:
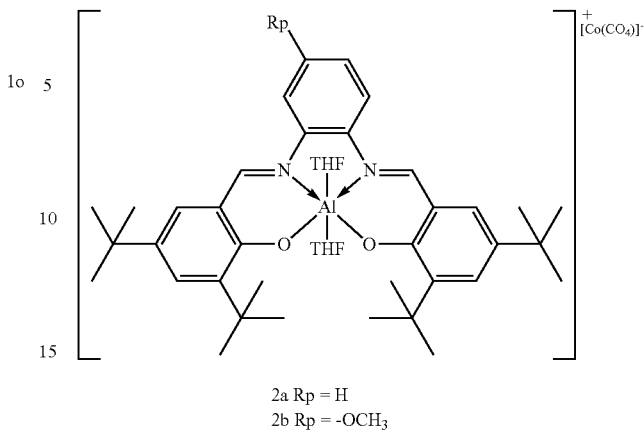
2a Rp = H
2b Rp = -OCH₃
In certain embodiments, the catalyst comprises a complex of formula 2c or 2d:
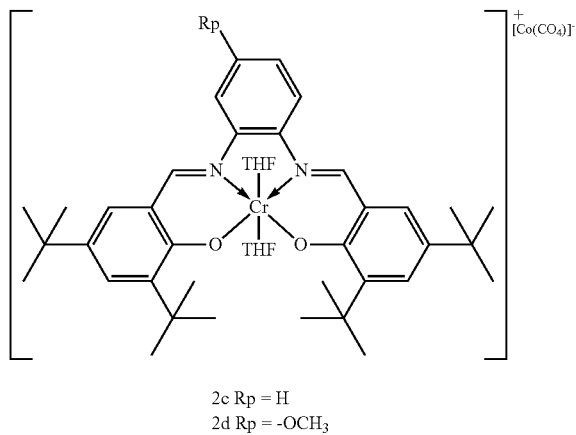
2c Rp = H
2d Rp = -OCH₃

In certain embodiments, the catalyst comprises a complex of formula 2e:
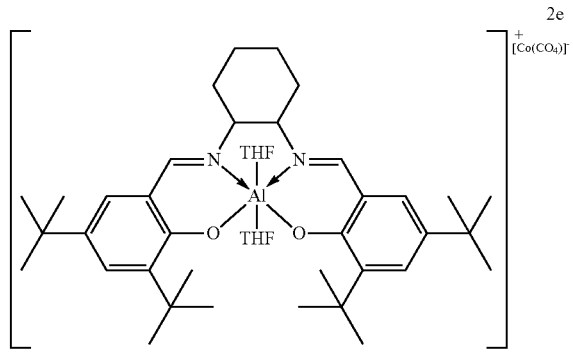
In certain embodiments, the catalyst comprises a complex of formula 2f:
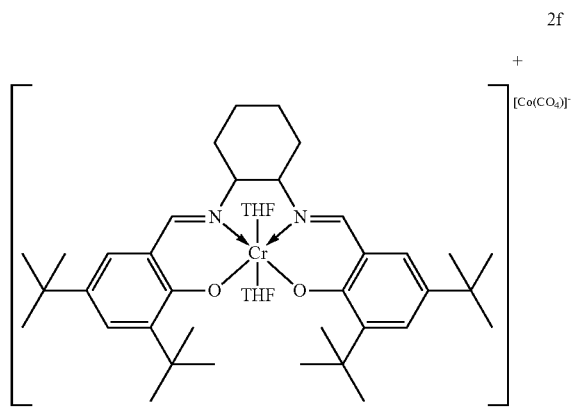
In certain embodiments, the catalyst comprises a complex of formula 3a:
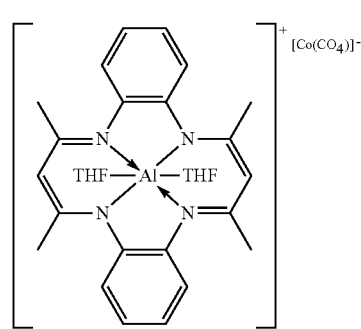
In certain embodiments, the catalyst comprises a complex of formula 3b:
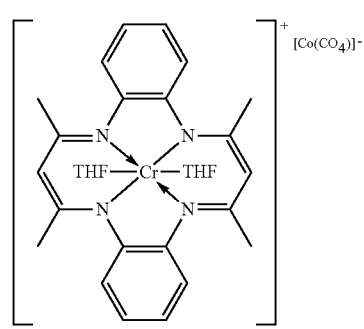

In certain embodiments, the catalyst comprises a complex of formula 4a:
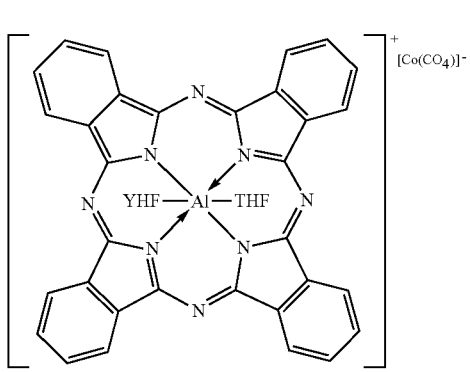
In certain embodiments, the catalyst comprises a complex of formula 4b:
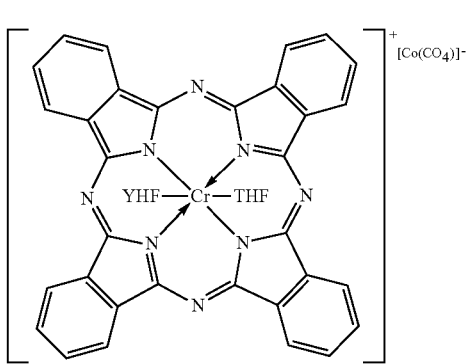
In certain embodiments, the catalyst comprises a complex of formula 5a:
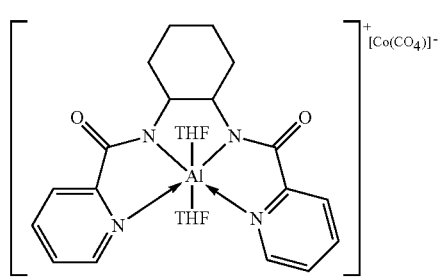
In certain embodiments, the catalyst comprises a complex of formula 5b:
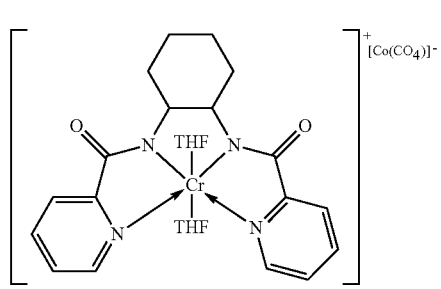

In certain embodiments, the catalyst comprises a complex of formula 7a:
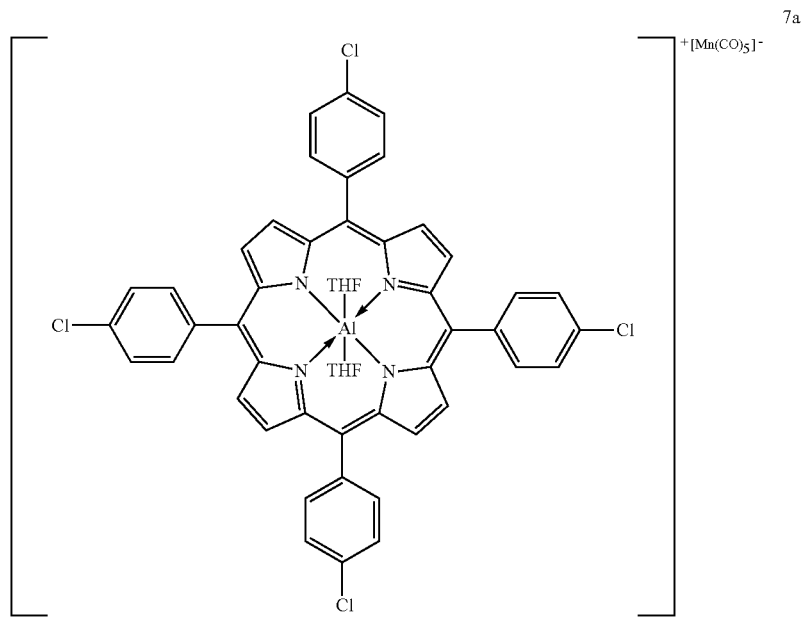
In certain embodiments, the catalyst comprises a complex of formula 7b:
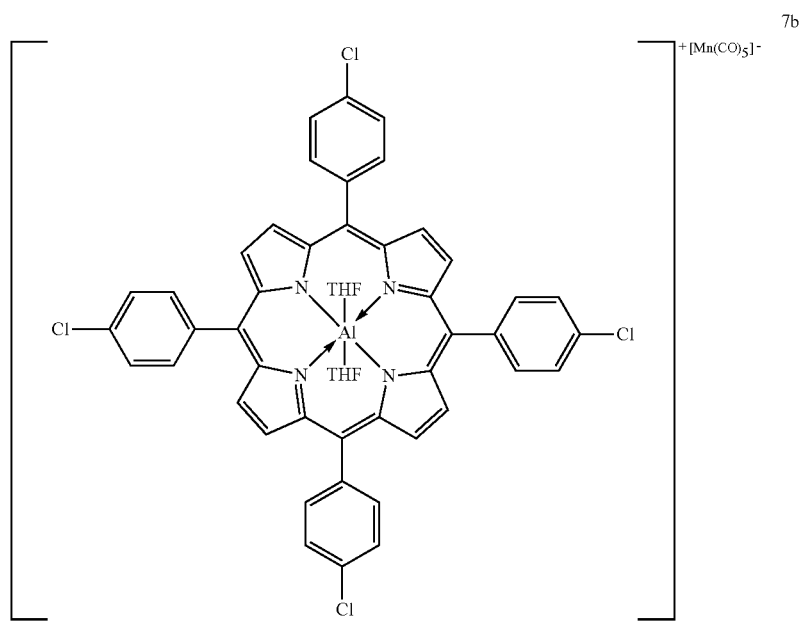

In certain embodiments, the catalyst comprises a complex of formula 9:

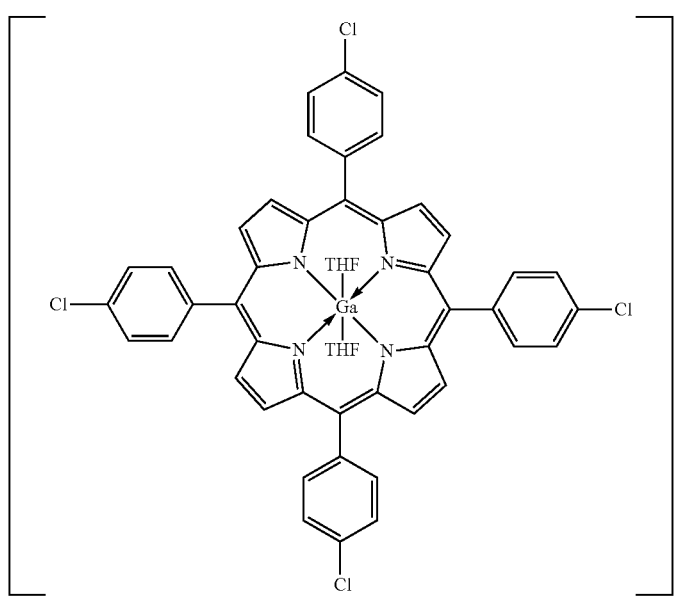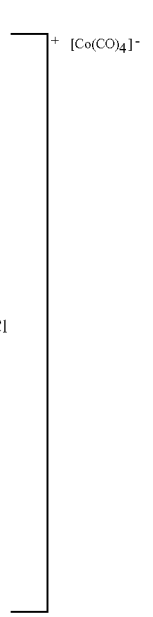

In certain embodiments, the catalyst comprises a complex of formula 10:

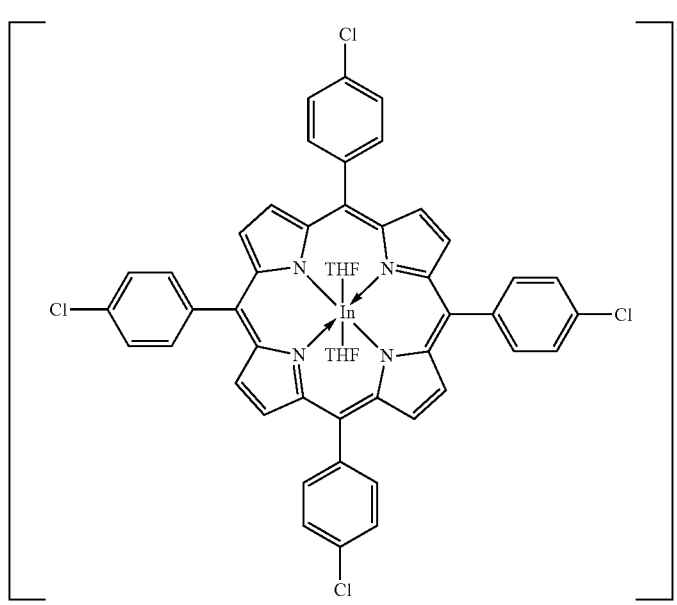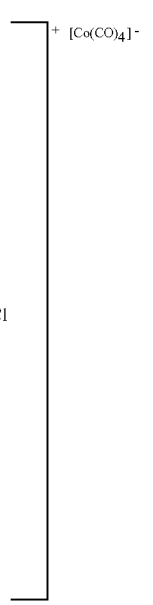

Additional examples of carbonylation catalysts can be found in U.S. Pat. No. 6,852,865, and in U.S. patent application Ser. Nos. 10/820,958 and 11/705,528; the entirety of each of which are hereby incorporated herein by reference.

Turning now to a more detailed description of the invention, it has been found that the catalysts described above can be used to successfully transform epoxides into succinic anhydride derivatives in a single reaction (i.e., in a single reaction vessel under one set of reaction conditions). Several aspects of the reaction conditions have been found to affect the outcome (e.g., the yield) of these processes including, but not limited to: the presence of a solvent, the concentration of the substrate, the amount of catalyst present, and the pressure and temperature at which the reaction is performed.

With respect to solvents, methods of the invention have been found to be improved by the presence of a solvent which includes a Lewis base. The term Lewis base as used herein refers to any nucleophilic species that is capable of donating an electron pair. As demonstrated in the Examples, we have found that the presence of suitable solvents can suppress the formation of polymeric side products and, in some cases, increase the rate and/or yield of the reaction.

In certain embodiments, the Lewis base is distinct from the epoxide. In other embodiments, the Lewis base is the epoxide (i.e., the reaction is performed in neat epoxide). Indeed, while the use of non-epoxide solvents may lead to higher yields, we have found that certain catalysts allow double carbonylation to be achieved in neat epoxide.

In certain embodiments, the solvent used will fully dissolve the epoxide substrate and provide a reaction mixture in which the catalyst employed is at least partially soluble. Suitable solvents may include ethers, ketones, aromatic hydrocarbons, halocarbons, esters, nitriles, and some alcohols. For example, without limitation, a suitable solvent may include: 1,4-dioxane; tetrahydrofuran; tetrahydropyran; dimethoxyethane; glyme; diethyl ether; t-butyl methyl ether; 2,5-dimethyl tetrahydrofuran; ethyl acetate; propyl acetate; butyl acetate; acetone; 2-butanone; cyclohexanone; toluene; acetonitrile; and difluorobenzene. In some embodiments, the solvent includes 1,4-dioxane, toluene, and/or dimethoxyethane. In one embodiment, solvent includes 1,4-dioxane. Mixtures of two or more of the above solvents are also useful, and in some cases may be preferred to a single solvent. For example, mixtures of toluene and 1,4-dioxane are useful.

In certain embodiments, we have found that Lewis bases of low to moderate polarity improve the performance of the reaction over polar solvents. Thus, in certain embodiments, the solvent may include a Lewis base which is less polar than 1,3-dioxane ($\epsilon$=dielectric constant at 20 C=13.6). In certain embodiments, the solvent includes a Lewis base which is less polar than ortho-difluorobenzene ($\epsilon$=13). In certain embodiments, the solvent includes a Lewis base which is less polar than meta-difluorobenzene ($\epsilon$=5). In certain embodiments, the solvent includes a Lewis base with substantially the same polarity as 1,4-dioxane ($\epsilon$=2.2).

In certain embodiments, we have found that Lewis bases of low to moderate electron donicity improve the performance of the reaction over strongly donating Lewis bases. Thus, in certain embodiments, the solvent may include a Lewis base with lower electron donicity than tetrahydrofuran. In certain embodiments, the solvent may include a Lewis base with lower electron donicity than 2-methyltetrahydrofuran. In certain embodiments, the solvent may include a Lewis base with lower electron donicity than 2,5-dimethyltetrahydrofuran. In certain embodiments, the solvent may include a Lewis base with higher electron donicity than difluorobenzene. In certain embodiments, the solvent may include a Lewis base with higher electron donicity than toluene. In certain embodiments, the solvent may include a Lewis base with substantially the same electron donicity as 1,4-dioxane.

It will be appreciated that while 1,4-dioxane appears to produce particularly high yields of anhydride when used in combination with various catalysts that are described in the Examples, other solvents and mixtures of solvents (including solvents and mixtures that are not explicitly disclosed) may be used with these catalysts. While some of these combinations may produce lower yields they remain within the scope of the present invention. It will also be appreciated that present invention is in no way limited to the representative catalysts that are exemplified in this application. In particular, now that we have demonstrated that high yield double carbonylation is possible through appropriate selection of catalyst and solvent, those skilled in the art will recognize that our teachings can be generalized to other catalyst/solvent combinations.

In general, highly polar, reactive or protic solvents are generally inferior or unsuitable for processes of the present invention. Inferior solvents include ionic liquids, chlorinated hydrocarbons, sulfolane, dimethylsulfoxide, formamide, pyridine, and the like. The solvent is preferably added in an amount sufficient to achieve an epoxide concentration of from about 0.1M to about 20M, for example from about 0.1M to about 5M or about from 0.5M to about 2M.

In certain embodiments, the reaction is conducted under a carbon monoxide atmosphere at a pressure from about 40 psi, to about 2500 psi. For example the carbon monoxide pressure may range from about 80 psi to about 1000 psi or from about 200 psi to about 800 psi. Optionally, the atmosphere under which the reaction is conducted can include other gasses. Such other gasses can include, for example, hydrogen, methane, nitrogen, carbon dioxide, air, and trace amounts of steam. The present invention also specifically encompasses processes in which other carbon monoxide-containing gas streams provide the atmosphere under which the reaction is conducted, the use of syngas, wood gas, or other carbon monoxide-containing industrial gas streams are specifically included.

Turning next to the effect of temperature, in certain embodiments the reaction temperature was found to affect the rate and outcome of processes of the invention. At higher temperatures the reaction proceeds more quickly than at lower temperatures, but the propensity to form reaction by-products increases. In particular, the production of ketone formed by isomerization of the epoxide substrate was found to increase with increasing temperature. This undesirable side-product can be minimized at higher reaction temperatures by performing the reaction at relatively high carbon monoxide pressures. In some cases therefore, the optimal temperature will be dependent upon the pressure at which the reaction is conducted. At high carbon monoxide pressures, e.g., greater than about 400 psi, elevated temperatures were found to be advantageous for the reaction (e.g., up to about 120 C). In some cases, the reaction may be conducted at a temperature ranging from about 40 C to about 80 C. To avoid ketone formation, the reaction mixture may be pressurized with CO while at a low temperature (e.g., <0 C) and heating is introduced only after CO has been allowed to contact the reaction mixture. If minimization of ketone is desired, the CO pressure may be applied for a period of time prior to heating the mixture (e.g., at least 5 minutes prior to heating).

Turning next to the catalysts, the catalyst is preferably present in an amount sufficient to allow the reaction process to be completed in a convenient time interval (e.g. less than about 24 hours, for example less than about 3 hours). In real terms this can require catalyst loadings ranging from about 0.0001 mole percent to about 20 mole percent based on the epoxide substrate. In certain embodiments, the catalyst loading can range from about 0.0001 mole percent to about 1 mole percent, e.g., from about 0.0001 mole percent to about 0.1 mole percent or from about 0.0001 mole percent to about 0.01 mole percent. In certain embodiments, the catalyst loading can range from about 0.001 mole percent to about 20 mole percent, e.g., from about 0.1 mole percent to about 1 mole percent or from about 0.067 mole percent to about 5 mole percent. In some embodiments, the catalyst loading is less than about 0.154 mole percent based on the epoxide substrate. In one such embodiment, the epoxide is ethylene oxide.

DEFINITIONS

The term 'carbocycle' as used herein means a saturated, unsaturated or aromatic ring system where all atoms comprising the ring(s) are carbon atoms. The term includes structures having more than one ring, such as fused ring systems, bridged ring systems and spirocycles. Carbocycles can include the carbon atoms of keto, imine, and oxime groups and can be substituted with one or more additional groups. If a specific number of carbons is recited with a specific appearance of the term carbocycle (e.g., 'up to $C_{12}$ carbocycle'), it is to be understood that the number refers only to those carbon atoms comprising the ring system and does not include any carbon atoms in substituents that may optionally be attached thereto.

The term 'heterocycle' as used herein means a saturated, unsaturated, or aromatic ring structure where one or more atoms in the ring is a heteroatom. The term includes structures having more than one ring, such as fused ring systems, bridged ring systems and spirocycles. The rings can also include the carbon atoms of keto, imine, and oxime groups and can be substituted with one or more additional groups. If a specific number of carbons is recited with a specific appearance of the term heterocycle (e.g., 'up to $C_{12}$ heterocycle'), it is to be understood that the number refers only to those carbon atoms comprising the ring system and does not include any carbon atoms in substituents that may optionally be attached thereto.

The term 'alkyl' as used herein means a branched or straight chain saturated hydrocarbon radical. The term is also meant to encompass alkyl groups where one or more hydrogen atoms are replaced by a halogen atom. Examples of alkyl groups include, but are not limited to: methyl, ethyl, n-propyl, n-hexyl, isobutyl, t-butyl, thexyl, 2-methyl pentyl, dichloromethyl, fluoromethyl, trifluoromethyl, pentafluoropropyl, and n-decyl.

The term 'alkenyl' as used herein means a branched or unbranched, mono- or poly-unsaturated hydrocarbon radical having one or more carbon-carbon double bonds. Each double bond can be substituted or unsubstituted, and can have cis or trans stereochemistry. The double bonds of polyunsaturated radicals can be conjugated or unconjugated and can include allenes. The term is also meant to encompass alkenyl groups where one or more hydrogen atoms are replaced by a halogen atom. Examples of alkenyl groups include, but are not limited to: vinyl, allyl, isoprenyl, cis-hex-3-enyl, trans-hex-3-enyl, trans, trans butane-1,3-dienyl, 3,3 dimethyl allenyl, 4-methyl hex-1-enyl, cis-but-2-enyl, and 4-methyl-1-hexenyl.

The term 'alkenyl' as used herein means a branched or unbranched, mono- or poly-unsaturated hydrocarbon radical having one or more carbon-carbon triple bonds. The term is also meant to encompass alkenyl groups where one or more hydrogen atoms are replaced by a halogen atom. Examples of alkynes include, but are not limited to propargyl, 2-butynyl, 5-hexynyl, and 2,2 dimethyl-3-butynyl.

Where a substituent is defined to encompass alkenyl or alkynyl substituents, it is to be understood that moieties having both carbon carbon double bonds and carbon carbon triple bonds (e.g., enynes) are also encompassed.

The present invention will be more specifically illustrated with reference to the following examples. Many of these examples are described in Rowley et al., *J. Am. Chem. Soc.* 2007 (129) 4948-4960 and in the supporting information published therewith. The entirety of this publication and its supporting information are hereby incorporated herein by reference.

EXAMPLES

Example 1

This example describes our initial attempts to effect high yield single reaction double carbonylation using catalysts and conditions we had previously reported for ring-expansive epoxide and lactone carbonylation. The results of these studies are summarized in Table 1, entries 1-4.

Although [(salph)Al(THF)$_2$]$^+$[Co(CO)$_4$]$^-$ (2 in Chart 1 and 2a elsewhere in the specification; salph=N,N'-bis(3,5-di-tert-butylsalicylidene)-1,2-phenylenediamine; THF=tetrahydrofuran) is the only catalyst which has been reported for both epoxide (Getzler et al., *J. Am. Chem. Soc.* 2002, 124, 1174-1175) and β-lactone (Getzler et al., *J. Am. Chem. Soc.* 2004, 126, 6842-6843) carbonylation, these two independent reactions were found to be orthogonal, such that the reaction conditions, particularly solvent (vide infra), which facilitated the first carbonylation, severely limited the second, and vice versa. For example, whereas lactone formation was facile in neat epoxide (entry 1) or ether solvents; non-polar conditions which favor anhydride formation severely reduced epoxide carbonylation without leading to any anhydride (entry 2).

TABLE 1

Single reaction double carbonylation of 1-butene oxide.[a]

| | | | product distribution (%) | | |
|---|---|---|---|---|---|
| entry | catalyst | solvent | lactone | polymer | anhydride |
| 1 | 2 | neat | 99 | — | — |
| 2 | 2 | toluene | 58[b] | — | — |
| 3 | 3 | neat | — | 93 | 7 |
| 4 | 3 | toluene | — | 67 | 33 |
| 5 | 1 | neat | — | 78 | 22 |
| 6 | 1 | toluene | — | — | 99 |

[a]Reaction conditions: 1.0 mol % catalyst, [epoxide] 1.8M in toluene or neat, 850 psi CO, 6 h, 60° C. Product distribution determined by $^1$H NMR spectra of crude reaction.
[b]Remainder is starting epoxide.

Chart 1. Epoxide carbonylation catalysts.

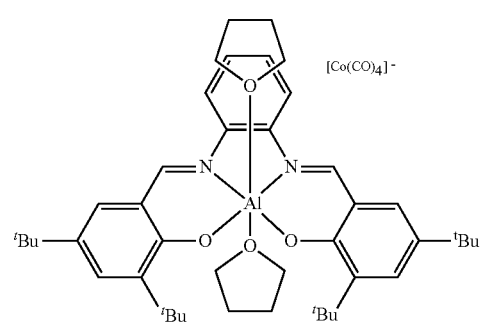

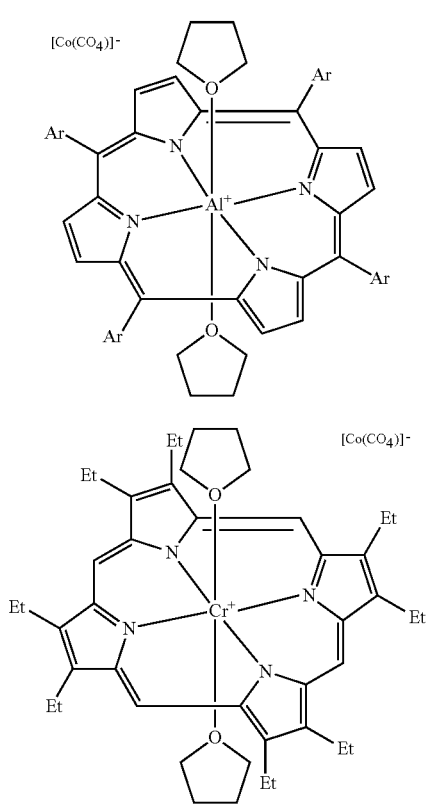

Ar = 4-Cl phenyl

[(OEP)Cr(THF)$_2$]$^+$[Co(CO)$_4$]$^-$ (3 in Chart 1 and 1o elsewhere in the specification; OEP=octaethylporphyrinato), the most active catalyst reported for epoxide carbonylation, was considered with the hope that inhibition by a non-polar solvent would be mediated by the exceptional activity of the catalyst. Under typical conditions and catalyst loadings (<0.03 mol %), β-lactone was the only product observed for this system. However, significantly increasing the amount of catalyst to 1 mol % resulted in very rapid lactone formation, followed by slower conversion of lactone to low molecular weight poly(lactone) and a small amount of anhydride (entry 3). Even under favorable (non-polar and diluted) conditions, polymer remains the major product (entry 4). Given the lackings of these previously reported catalysts, conditions, and permutations thereof, it was clear that to effect high yield anhydride formation, the efficient double carbonylation of epoxides would require either a new catalyst, a new solvent, or both.

The following examples describe exemplary catalyst/solvent combinations which we have shown can be used to effect high yield double carbonylation of epoxides. It is to be understood that these combinations are exemplary and that, in view of the representative teachings that are provided in this disclosure, those skilled in the art will be able to identify a variety of alternative combinations.

Example 2

This example describes an exemplary bimetallic catalyst [(ClTPP)Al(THF)$_2$]$^+$[Co(CO)$_4$]$^-$ (1 in Chart 1 and 1c elsewhere in the specification; ClTPP=meso-tetra(4-chlorophenyl)porphyrinato) which rapidly catalyzed both epoxide and lactone carbonylation. While some low-molecular-weight polymer was formed in the absence of solvent (Table 1, entry 5), addition of solvent resulted in the first high yield single reaction double carbonylation of epoxide to succinic anhydride (entry 6).

Though double carbonylation proceeded at 25° C., increasing the temperature to 90° C. accelerated the reaction without decreasing selectivity Anhydrides were formed cleanly at pressures as low as 100 psi; however, at lower pressures and in the absence of CO, 1c catalytically isomerizes epoxides to ketones.

In order to assess the impact of solvent on the rate of reaction, we attempted epoxide double carbonylation in a range of solvents. Conversion to succinic anhydride varied widely with solvent, as illustrated by a representative selection of solvents in FIG. 1. Hexane was a poor solvent, yielding mostly polymer. Acyclic monofunctional ether solvents such as diethyl ether were effective for double carbonylation, though polymer remained a significant by-product. Moderately coordinating, cyclic or multifunctional ether solvents resulted in the cleanest reactions. In particular, the double carbonylation was distinctively rapid in 1,4-dioxane. Strongly coordinating solvents such as acetonitrile severely inhibited lactone carbonylation. Additional solvent experiments are described in the Examples that follow.

Example 3

Figure 2A:
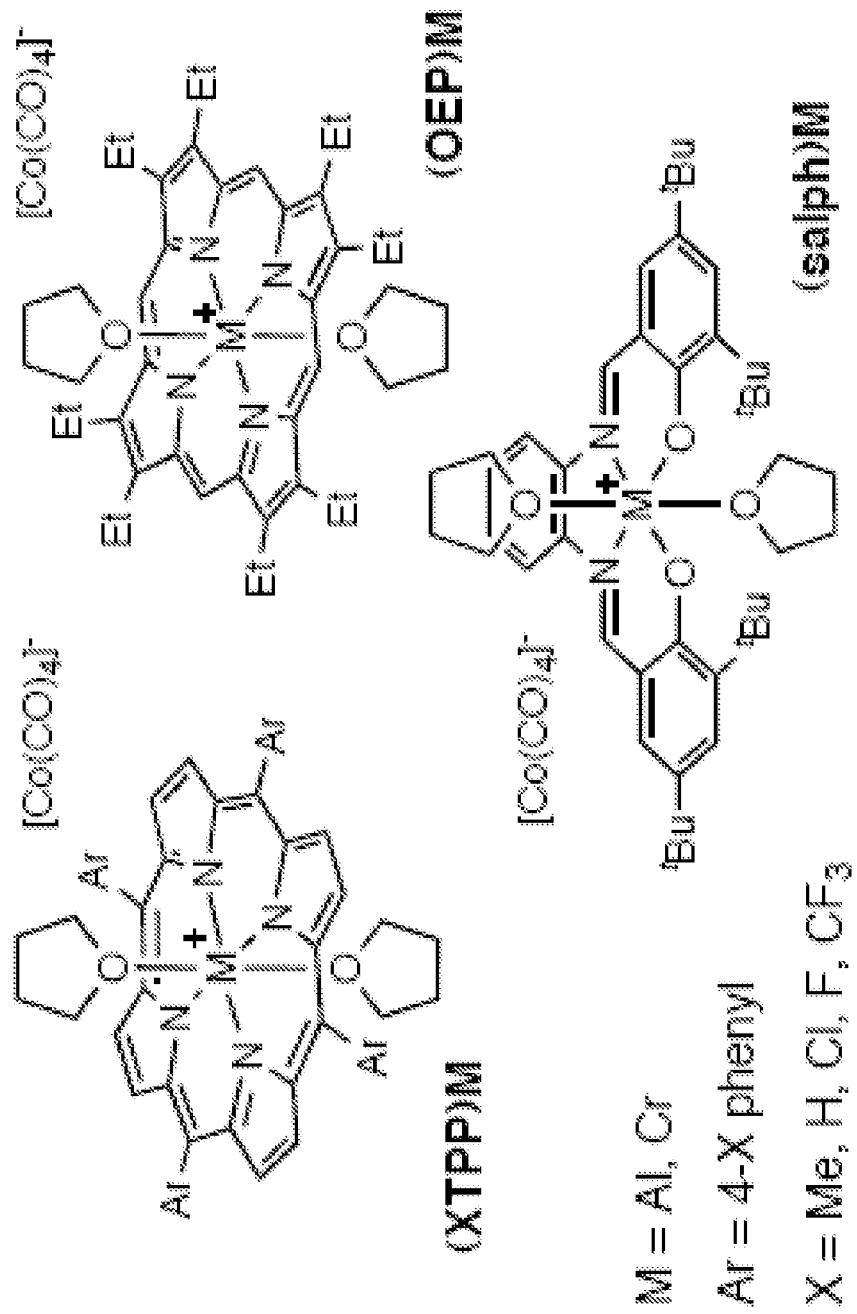
FIG. 2A illustrates the structure of certain catalysts used in the experiments that are summarized in FIG. 2B.
Figure 2B:
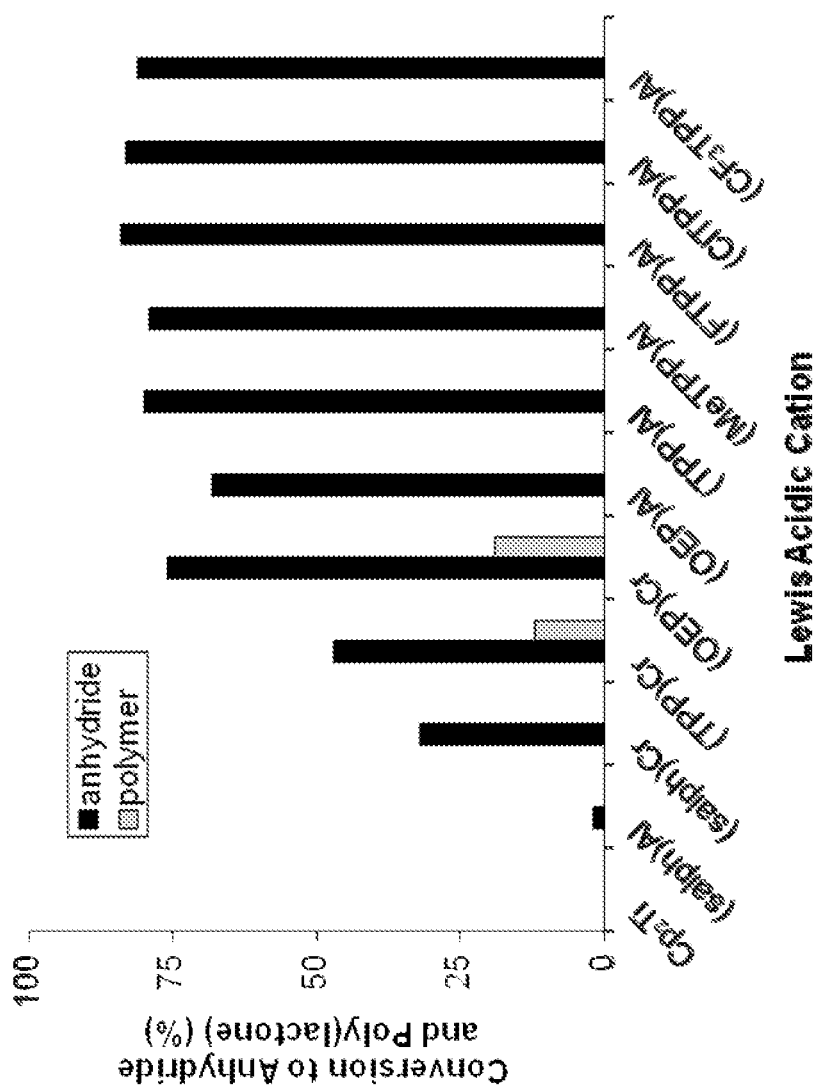
FIG. 2B illustrates the results of double carbonylation experiments in 1,4-dioxane using different catalysts. Reaction conditions: 2 mmol 1,2-epoxybutane in 1 mL dioxane, 0.2 mol % catalyst, 850 psi CO, 2 h, 90° C. Product distribution determined by $^1$H NMR spectrum of crude reaction mixture. All catalysts, except Cp$_2$Ti, completely converted epoxide to lactone (not shown). Subsequent conversion of lactone to anhydride (black) and polymer (gray) for other catalysts is shown.

This example describes other exemplary catalysts of the general form [(ligand)M(THF)$_2$]$^+$[Co(CO)$_4$]$^-$ which are capable of high yield double carbonylation in 1,4-dioxane (FIG. 2A). As shown in FIG. 2B, under these conditions Cp$_2$Ti (Cp=cyclopentadienyl) only converted 6% of the epoxide to lactone, and made no anhydride. The only catalyst previously reported for epoxide and β-lactone carbonylation, (salph)Al (see also Example 1 where it was tested in neat epoxide and toluene), was slow for double carbonylation. Interestingly, the chromium analog, (salph)Cr, was much faster than (salph)Al. (TPP)Cr and (OEP)Cr (see also Example 1 where it was tested in neat epoxide and toluene) were also capable of yielding significant amounts of anhydride though these porphyrin Cr complexes gave poly(lactone) as a significant byproduct. Significantly, the aluminum analogs, (TPP)Al and (OEP)Al gave much cleaner yields of anhydride. Relative to the tetraphenylporphyrin (TPP) ligands, the more electron-donating octaethylporphyrin (OEP) ligand diminished the activity of the Al complexes.

Among the catalysts we tested in 1,4-dioxane, tetraphenylporphyrin aluminum cations (Lewis acid component of catalyst) appeared to be the most effective for clean, catalytic, double carbonylation of epoxides to succinic anhydrides. A series of catalysts with substituted porphyrin phenyl rings were therefore synthesized (XTPP=meso-tetra(4-X-phenyl)porphyrinato). As shown in FIG. 2B, this substitution had little effect on the activity of the catalysts. Cl was the most economical para substituent, and this substitution imparted greater crystallinity to the isolated complex.

Example 4

This example illustrates the versatility of the single reaction double carbonylation with a variety of functionalized epoxides (Table 2). Substrate to catalyst ratios were adjusted to achieve complete conversion of 1-2 mmol of epoxide in 3 h at 90° C.; longer reaction times were used if more than 2 mol % catalyst was required to complete the reaction in 3 h. Conversion to anhydride is reported to indicate the high selectivity of the reaction. In most cases, isolation is straightforward, only requiring removal of solvent and catalyst. As shown in Table 2, the reaction worked with ethylene oxide (4) and epoxides with pendant alkyl groups (entries 2-6). Substrates with ether side chains were less active, but high yields and selectivity were retained (entries 7-9). Surprisingly, good conversion to anhydride was obtained with an unprotected alcohol, although the presence of incompatible alcohol and anhydride groups in the product results in lower isolated yields (entry 10). Ester functionality was well tolerated (entry 11), except in the case of glycidyl esters, where isomerization to γ-lactone was favored over double carbonylation. Anhydrides with nitrile and amide side-chains were also synthesized in high yields (entries 12 and 13), although, in the presence of an amide, carbonylation of the lactone intermediate was very slow, presumably due to competitive coordination with the Lewis acid. Epoxides with pendant alkenes exhibited varied activity depending on chain length (entries 14 and 15). Aryl groups were also tolerated (entries 16 and 17), but styrene oxide (36) was run at lower temperature for a longer time to avoid thermal decarboxylation of the lactone intermediate. Substrates with more than one epoxide can undergo multiple double carbonylations; for example, 1,2,7,8-diepoxyoctane (38) was quadruply carbonylated to give the bis(succinic anhydride), 39, in good yield.

TABLE 2

Double carbonylation of functionalized epoxides.[a]

| entry | epoxide | epoxide/1 | anhydride | yield (%)[b] |
|---|---|---|---|---|
| 1 | 4 | 1500 | 5 | 98 (93) |
| 2 | 6 | 650 | 7 | 99 (89) |
| 3 | 8 | 250 | 9 | 99 (80) |
| 4 | 10 | 250 | 11 | 97 (88) |
| 5 | 12 | 300 | 13 | 99 (93) |
| 6 | 14 | 150 | 15 | 97 (82) |

TABLE 2-continued
Double carbonylation of functionalized epoxides.[a]
| entry | epoxide | epoxide/1 | anhydride | yield (%)[b] |
|---|---|---|---|---|
| 7 | 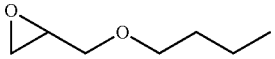<br>16 | 100 | 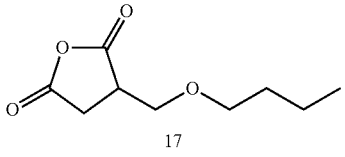<br>17 | 99 (80) |
| 8 | 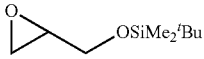<br>18 | 250 | 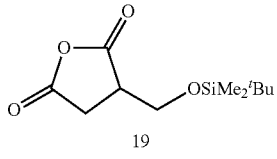<br>19 | 98 (83) |
| 9 | 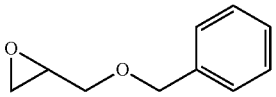<br>20 | 50 | 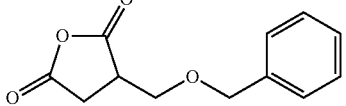<br>21 | 96 (87) |
| 10 | 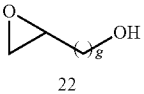<br>22 | 150 | 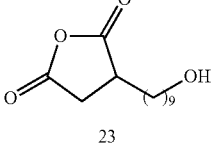<br>23 | 93 (72) |
| 11 | 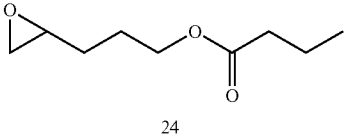<br>24 | 300 | 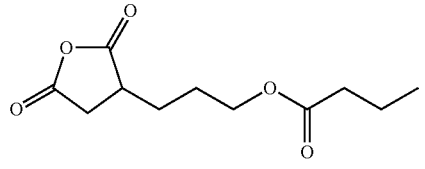<br>25 | 99 (89) |
| 12 | 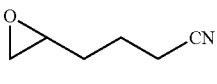<br>26 | 100 | 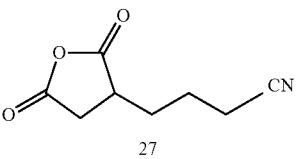<br>27 | 99 (77) |

TABLE 2-continued

Double carbonylation of functionalized epoxides.[a]

| entry | epoxide | epoxide/1 | anhydride | yield (%)[b] |
|---|---|---|---|---|
| 13 | 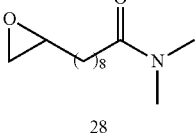 28 | 20 | 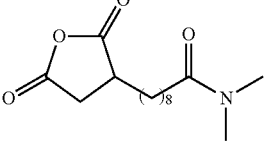 29 | 98 (79)[c] |
| 14 | 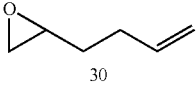 30 | 50 | 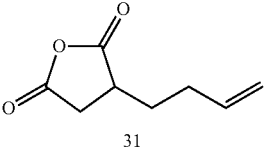 31 | 90 (82)[c] |
| 15 | 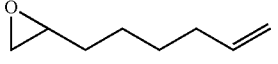 32 | 100 | 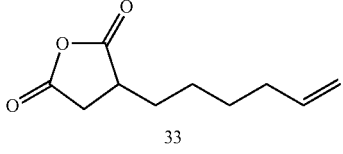 33 | 99 (85) |
| 16 | 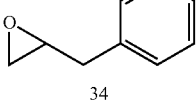 34 | 100 | 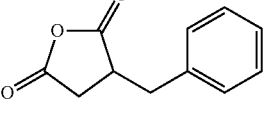 35 | 99 (78) |
| 17 | 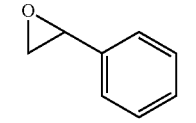 36 | 50 | 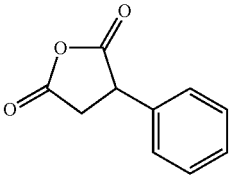 37 | 93 (72)[d] |
| 18 | 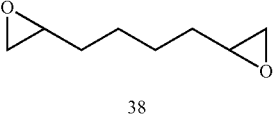 38 | 150 | 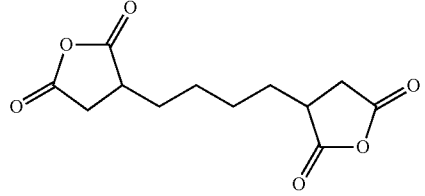 39 | 98 (89) |

[a]Unless specified otherwise, reactions run for 3 h at 850 psi CO and 90 C. in 1,4-dioxane (1.8M epoxide).
[b]Yield of anhydride determined by $^1$H NMR spectroscopy of crude reaction mixture and verified by internal standard; corresponding lactone and ketone[31] were the only other products detected. Unoptimized isolated yields in parentheses.
[c][epoxide] = 1.0M at 90 C. for 24 h.
[d][epoxide] = 1.0M at 50 C. for 12 h.

1,2-Disubstituted epoxides were carbonylated to the corresponding succinic anhydrides with retention of relative stereochemistry. cis-Epoxides were carbonylated to cis-anhydrides via the trans-lactones, and trans-epoxides were carbonylated to the trans-anhydrides via cis-lactones (Table 3).

TABLE 3

Double carbonylation of disubstituted epoxides.[a]

| entry | epoxide | epoxide/1 | anhydride | yield (%)[b] | trans:cis[b] |
|---|---|---|---|---|---|
| 1[c] | 40 | 100 | 41 | 95 | 1:20 |
| 2 | 42 | 200 | 43 | 99 | >100:1 |
| 3 | 44 | 75 | 45 | 99 | >100:1 |
| 4 | 46 | 100 | 47 | 99 | >100:1 |

[a]All reactions run for 24 h at 850 psi CO and 50° C. in 1,4-dioxane (1.8M epoxide).
[b]Conversion to anhydride and relative stereochemistry determined from the $^1$H NMR spectroscopy of crude reaction mixture; lactone and ketone were the only other products detected.
[c][epoxide] = 1.0M in 1,4-dioxane.

At elevated temperatures, some epimerization of the anhydride occurred in the presence of catalyst; however, lower temperatures and thus longer reaction times afforded either cis- or trans-succinic anhydrides (entries 1 and 2) with good stereochemical purity. The cis-anhydride 41 was not formed as easily as the trans-anhydride 43, and had to be run at lower concentration to avoid poly(lactone) formation. Increasing steric bulk decreased the rate of carbonylation, but relative stereochemical purity was preserved (entry 3). Using this reaction, a class of natural product diacids are readily accessible via hydrolysis of unsymmetrical succinic anhydrides, such as 47.

TABLE 4

Double carbonylation of enantiomerically pure epoxides.[a]

| entry | epoxide | ee (%) | epoxide/1 | T (° C.) | anhydride | yield (%)[b] | ee (%)[c] |
|---|---|---|---|---|---|---|---|
| 1 | (R)-6 | >99 | 650 | 90[d] | (S)-7 | 97 | 97 |

TABLE 4-continued

Double carbonylation of enantiomerically pure epoxides.[a]

| entry | epoxide | ee (%) | epoxide/1 | T (° C.) | anhydride | yield (%)[b] | ee (%)[c] |
|---|---|---|---|---|---|---|---|
| 2 | (R)-6 | >99 | 300 | 50 | (S)-7 | 99 | >99 |
| 3 | (S)-10 | >99 | 300 | 50 | (R)-11 | 99 | >99 |
| 4 | (R)-20 | >99 | 100 | 50 | (S)-21 | 96 | 97 (>99)[e] |

[a] Unless specified otherwise, reactions run for 24 h at 850 psi CO in 1,4-dioxane (1.8M epoxide).
[b] Conversion to anhydride determined by $^1$H NMR spectroscopy of reaction mixture; lactone and ketone were the only other products detected.
[c] Determined by chiral GC or HPLC of crude product.
[d] Reaction run for 3 h.
[e] Product recrystallized from ether, 87% isolated yield.

Succinic anhydrides and succinate derivatives with excellent enantiomeric purity were readily accessed via double carbonylation (Table 4).

(S)-Methylsuccinic anhydride, (S)-7, was rapidly obtained from (R)-propylene oxide, (R)-6, with a slight loss of enantiomeric purity at 90° C. (entry 1), but at 50° C., greater than 99% enantiomeric excess is maintained through clean inversion of the stereocenter (entry 2). Likewise, larger alkyl and functionalized epoxides were carbonylated to yield anhydrides with ≥97% ee (entries 3-4). Thus, double carbonylation yields anhydrides as useful intermediates for asymmetric synthesis.

Example 5

This example describes experiments that were performed to further investigate the effects of solvent on the double carbonylation reaction when performed with catalyst 1c of Example 2. Propylene oxide (PO) was reacted with carbon monoxide in a variety of solvents and the reaction was monitored by in situ IR spectroscopy. For every solvent studied, the double carbonylation occurred in two distinct and non-overlapping stages; however, the rate of each stage varied greatly as a function of solvent.

Figure 3:
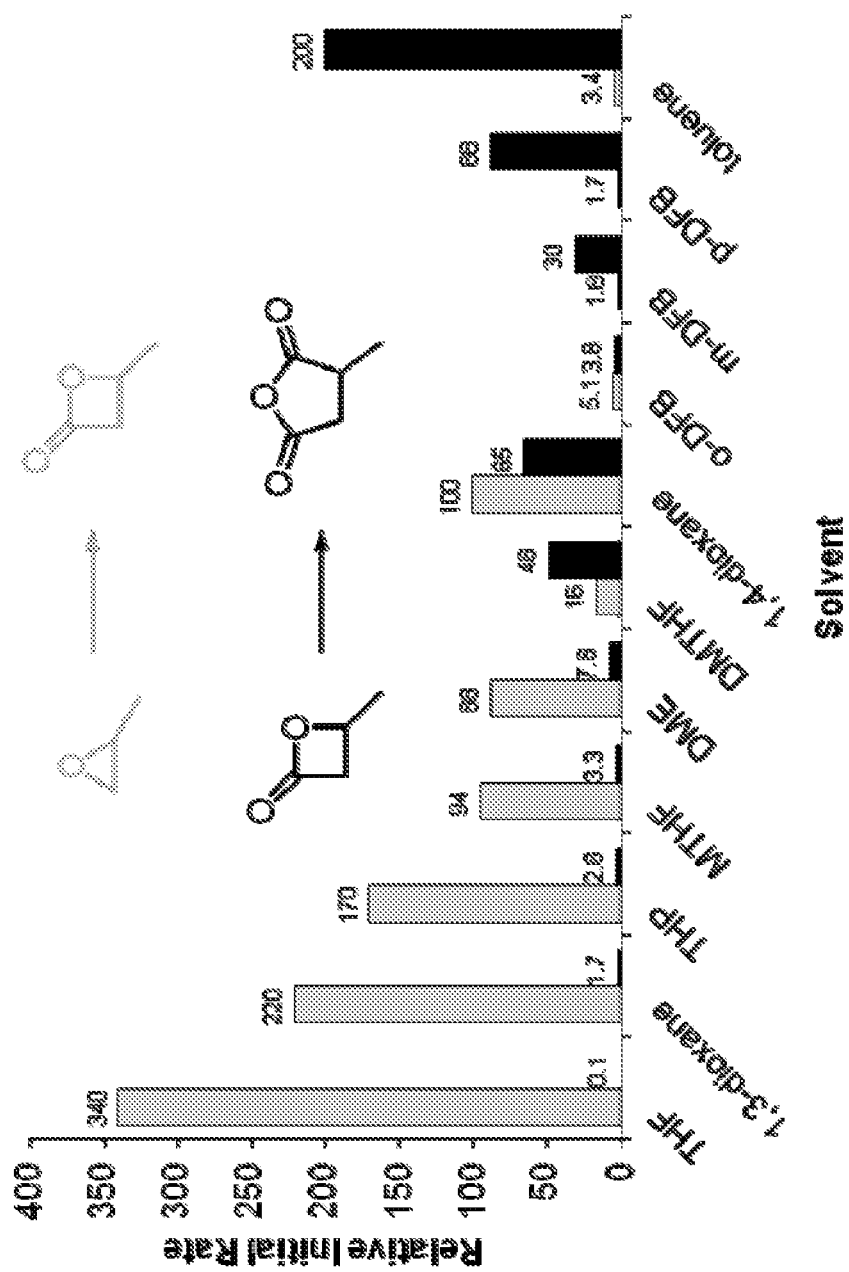
FIG. 3 compares the relative initial rates for epoxide (gray) and lactone (black) carbonylation using catalyst 1c as a function of solvent. Reactions monitored with in situ IR spectroscopy ($v_{C=O}$=1827 cm$^{-1}$). [PO]$_0$=1.0 M or [BBL]$_0$=1.0 M, [catalyst 1c]=2.0 mM, P$_{CO}$=850 psi, T=40° C.

As seen in FIG. 3, the rate of epoxide carbonylation slowed with increasing sterics and decreasing donicity of the substituted THF solvents: THF, 2-methyltetrahydrofuran (MTHF), 2,5-dimethyltetrahydrofuran (DMTHF). Similar activity was seen with the moderately donating tetrahydropyran (THP), 1,2-dimethoxyethane (DME), and dioxane, but the reaction was very slow in poorly coordinating toluene and difluorobenzene (DFB).

For lactone carbonylation, the trend was found to be reversed, highlighting the differences between these two stages (FIG. 3). Thus, poorly coordinating solvents (DMTHF, DFB, and toluene) generally resulted in uninhibited lactone ring opening; whereas the strongly Lewis basic, coordinating solvents severely slowed anhydride formation, such that a low yield of anhydride was produced in THF.

Based on these results, we hypothesized that in order to find a solvent system that has comparable rates for both carbonylations, a possible solution might be to use a mixture of solvents, or a solvent with intermediate donicity. For example, we have found that 1,4-dioxane is able to facilitate both epoxide and lactone carbonylation (FIG. 3). 1,4-Dioxane was also found to be far more active than an optimized mixture of the two solvent extremes.

The origin of the enhanced activity seen for both stages in 1,4-dioxane does not appear to result solely from its intermediate donicity. Instead, the low dipole moment of 1,4-dioxane appears to be an additional factor. The importance of this solvent polarity, separate from donicity, is illustrated by comparing the rates of carbonylation in the isomers of difluorobenzene (FIG. 3). In most respects ortho-, meta-, and para-difluorobenzene (o-DFB, m-DFB, p-DFB) are similar solvents, however they vary widely in polarity ($\epsilon$=13, 5, and 2 respectively, see Wohlfarth, C. In *CRC Handbook of Chemistry and Physics;* 76th ed.; Lide, D. R., Ed.; CRC Press: New York, 1995, pp 6-149), thus differences in rate in these solvents may be primarily attributed to the difference in polarity of each isomer.

Epoxide carbonylation was comparably slow in all three DFB isomers, (as expected from their poor donicity) with little change thus attributable to differences in polarity. Donicity appears to have a greater influence than polarity on the rate of epoxide carbonylation. For lactone carbonylation, however, markedly different rates are observed in each isomer of DFB. o-DFB, the most polar isomer, is an extremely slow solvent for lactone carbonylation; m-DFB is less polar and exhibits an increased rate; and p-DFB is non-polar and the best isomer for rapid lactone carbonylation (FIG. 3). Based solely on their poor donicity, all three isomers should be competent solvents for lactone carbonylation; instead we see a clear trend of increasing rate with decreasing solvent polarity.

To test this effect of polarity with dioxane, we predicted that 1,3-dioxane ($\epsilon=13.6$), which is significantly more polar than 1,4-dioxane ($\epsilon=2.2$), would result in slow lactone carbonylation, comparable to the other more polar ether solvents. In fact, this was exactly what we observed, confirming that non-polar solvents facilitate lactone carbonylation (FIG. 3).

Overall, it appears that the rate of epoxide carbonylation is primarily dependent on solvent donicity; whereas, the rate of lactone carbonylation is dependent on both solvent donicity and polarity. Without wishing to be limited to any particular theory, the ability of 1,4-dioxane to function as a solvent for both epoxide and lactone carbonylation may be explained in terms of its combination of these properties. It retains enough Lewis basic character to assist in ring closing to form lactone, while not significantly inhibiting the subsequent ring opening of lactone. Additionally, its low polarity does not retard epoxide carbonylation, but accelerates lactone carbonylation, due to a non-polar environment, which may favor the transition of catalyst from an ionic pair to a formally neutral intermediate upon ring opening of lactone. Thus, endowed with the proper combination of donicity and polarity, 1,4-dioxane enables the rapid and efficient double carbonylation of epoxides in the presence of various catalysts described herein including catalyst 1c.

Example 6

This example describes experiments in which isobutylene oxide or α-butylene oxide were reacted with carbon monoxide in neat epoxide or toluene in the presence of two different catalysts. Table 5 reports the catalyst loading (expressed as molar ratio of epoxide to catalyst) and anhydride yield for each catalyst/solvent combination.

TABLE 5

Single reaction double carbonylation.[a]

| entry | epoxide | ligand[b] | solvent | [catalyst] | yield (%) |
|---|---|---|---|---|---|
| 1 | isobutylene oxide | TMP | neat | 131 | 58 |
| 2 | isobutylene oxide | TMP | neat | 519 | 37 |
| 3 | α-butylene oxide | TMP | neat | 110 | 31 |
| 4 | α-butylene oxide | TMP | neat | 627 | 48 |
| 5 | α-butylene oxide | TMP | toluene | 73 | >95 |
| 6 | α-butylene oxide | ClTPP | toluene | 50 | >95 |

[a]Reaction conditions: [epoxide] 1M (toluene), 890 psi CO, 1.5 h, 70-100 C. Product distribution determined by ¹H NMR spectra of crude reaction.
[b]Catalyst = [(ligand)Al(THF)₂]⁺[Co(CO)₄]⁻, TMP = tetramesitylporphyrin, ClTPP = meso-tetra(4-chlorophenyl)porphyrinato.

Example 7

This example describes experiments in which α-butylene oxide was reacted with carbon monoxide in the presence of different amounts of 1,4-dioxane and catalyst. Table 6 reports the catalyst loading (expressed as molar ratio of epoxide to catalyst), solvent concentration (expressed as molar ratio of solvent to epoxide) and anhydride yield for each experiment. Entries 1-3 show that increased catalyst loading leads to reduced yield. Entries 3-5 show that increased solvent concentration leads to increased yield.

TABLE 6

Single reaction double carbonylation.[a]

| entry | epoxide | ligand[b] | solvent | [catalyst] | [solvent] | yield (%) |
|---|---|---|---|---|---|---|
| 1 | a-butylene oxide | ClTPP | 1,4-dioxane | 500 | 6.24 | 74 |
| 2 | a-butylene oxide | ClTPP | 1,4-dioxane | 304 | 6.24 | 85 |
| 3 | a-butylene oxide | ClTPP | 1,4-dioxane | 254 | 6.24 | 92 |
| 4 | a-butylene oxide | ClTPP | 1,4-dioxane | 198 | 2.94 | 90 |
| 5 | a-butylene oxide | ClTPP | 1,4-dioxane | 200 | 1.00 | 62 |

[a]Reaction conditions: 620 psi CO, 18 h, 90 C. Product distribution determined by ¹H NMR spectra of crude reaction.
[b]Catalyst = [(ligand)Al(THF)₂]⁺[Co(CO)₄]⁻, ClTPP = meso-tetra(4-chlorophenyl)porphyrinato.

Example 8

This example describes experiments in which α-butylene oxide was reacted with carbon monoxide in 1,4-dioxane in the presence of different catalysts. Table 7 reports the catalyst loading (expressed as molar ratio of epoxide to catalyst) and anhydride yield for each experiment.

TABLE 7

Single reaction double carbonylation.[a]

| entry | epoxide | ligand[b] | solvent | [catalyst] | yield (%) |
|---|---|---|---|---|---|
| 1 | α-butylene oxide | ClTPP | 1,4-dioxane | 511 | 71 |
| 2 | α-butylene oxide | MeTPP | 1,4-dioxane | 654 | 55 |
| 3 | α-butylene oxide | FTPP | 1,4-dioxane | 509 | 78 |

[a]Reaction conditions: [epoxide] 1.8M, 500 psi CO, 2 h, 90 C. Product distribution determined by ¹H NMR spectra of crude reaction.
[b]Catalyst = [(ligand)Al(THF)₂]⁺[Co(CO)₄]⁻, XTPP = meso-tetra(4-X-phenyl)porphyrinato.

Example 9

This example describes experiments in which α-butylene oxide was reacted with carbon monoxide in different solvents in the presence of the same catalyst. Table 8 reports the catalyst loading (expressed as molar ratio of epoxide to catalyst) and anhydride yield for each experiment.

TABLE 8

Single reaction double carbonylation.[a]

| entry | epoxide | ligand[b] | solvent | [catalyst][c] | yield (%) |
|---|---|---|---|---|---|
| 1 | α-butylene oxide | ClTPP | CH₃CN | 605 | — |
| 2 | α-butylene oxide | ClTPP | CDCl₃ | 500 | — |
| 3 | α-butylene oxide | ClTPP | 1,2-difluorobenzene | 510 | 12 |
| 4 | α-butylene oxide | ClTPP | hexane | 500 | 16 |
| 5 | α-butylene oxide | ClTPP | acetone | 505 | 17 |

TABLE 8-continued

Single reaction double carbonylation.[a]

| entry | epoxide | ligand[b] | solvent | [catalyst][c] | yield (%) |
|---|---|---|---|---|---|
| 6 | α-butylene oxide | ClTPP | tetrahydrofuran | 529 | 18 |
| 7 | α-butylene oxide | ClTPP | cyclohexanone | 500 | 18 |
| 8 | α-butylene oxide | ClTPP | 2-isopropoxypropane | 500 | 36 |
| 9 | α-butylene oxide | ClTPP | ether | 495 | 38 |
| 10 | α-butylene oxide | ClTPP | ethyl acetate | 500 | 42 |
| 11 | α-butylene oxide | ClTPP | 1,2-dimethoxyethane | 509 | 43 |
| 12 | α-butylene oxide | ClTPP | methyl tert-butyl ether | 500 | 43 |
| 13 | α-butylene oxide | ClTPP | tetrahydropyran | 500 | 45 |
| 14 | α-butylene oxide | ClTPP | toluene | 540 | 47 |
| 15 | α-butylene oxide | ClTPP | diglyme | 500 | 53 |
| 16 | α-butylene oxide | ClTPP | 1,4-dioxane | 510 | 59 |

[a]Reaction conditions: [epoxide] 1.8M, 850-900 psi CO, 2 h, 90 C. Product distribution determined by $^1$H NMR spectra of crude reaction.
[b]Catalyst = [(ligand)Al(THF)$_2$]$^+$[Co(CO)$_4$]$^-$, ClTPP = meso-tetra(4-chloropheny)porphyrinato.
[c]Molar ratio of epoxide to catalyst. For entries 2, 4, 7, 12, 13 and 15 these are the predicted, not actual values.

Example 10

This example describes experiments in which α-butylene oxide was reacted with carbon monoxide in THF in the presence of a gallium based catalyst. Table 9 reports the catalyst loading (expressed as molar ratio of epoxide to catalyst) and anhydride yield for each experiment.

TABLE 9

Single reaction double carbonylation.[a]

| entry | epoxide | ligand[b] | solvent | [catalyst] | yield (%) |
|---|---|---|---|---|---|
| 1 | α-butylene oxide | TPP | tetrahydrofuran | 200 | 14 |
| 2 | α-butylene oxide | TPP | 1,2-dimethoxyethane | 500 | 17 |
| 3 | α-butylene oxide | TPP | 1,4-dioxane | 500 | 38 |

[a]Reaction conditions: [epoxide] 1.8M, 600 psi CO, 2 h, 90 C. Product distribution determined by $^1$H NMR spectra of crude reaction. Entry 1 was obtained with [epoxide] 1.5M, 800 psi CO, 3 h, 90 C.
[b]Catalyst = [(ligand)Ga(THF)$_2$]$^+$[Co(CO)$_4$]$^-$, TPP = tetraphenylporphyrin.

Example 11

The following example describes materials and general methods that were used in some of the preceding examples.

Materials

Carbon monoxide (research grade) was purchased from Matheson and used without further purification. 1,4-Dioxane, 1,3-dioxane, tetrahydropyran, tetrahydrofuran, 2-methyltetrahydrofuran, 2,5-dimethyltetrahydrofuran, diethyl ether, and 1,2-dimethoxyethane were vacuum transferred from purple Na/benzophenone. Hexanes and toluene were dried and deoxygenated on columns of alumina and Q5 copper, respectively. Diethyl ether and methylene chloride were dried on columns of alumina and degassed via repetitive freeze-pump-thaw cycles (FPT). Difluorobenzene, ethyl acetate, acetone, and acetonitrile were dried over 4 Å molecular sieves and vacuum transferred after FPT. Epoxides were stirred for one week over CaH$_2$, degassed by FPT, and vacuum distilled, except 10,11-epoxyundecan-1-ol (22) N,N-dimethyl-10,11-undecylamide (28), which were dried over CaH$_2$, filtered, and degassed by stirring under dynamic vacuum (0.1 torr). Ethylene oxide (4), propylene oxide (6), 1,2-epoxybutane (8), 1,2-epoxyhexane (10), 1,2-epoxydodecane (12), n-butyl glycidyl ether (16), tert-butyldimethylsilyl glycidyl ether (18), benzyl glycidyl ether (20), 1,2-epoxy-5-hexene (30), 1,2-epoxy-7-octene (32), (2,3-epoxypropyl)benzene (34), styrene oxide (36), 1,2,7,8-diepoxyoctane (38), β-propiolactone, β-butyrolactone (BBL), 4-nitrophenylisocyanate, and meta-chloroperoxybenzoic acid (mCPBA) were purchased from Aldrich. cis-2,3-Epoxybutane (40), and trans-2,3-epoxybutane (42), were purchased from GFS Chemicals. iso-Butylene oxide was purchased from TCI America. Co$_2$(CO)$_8$ and octaethylporphyrin were purchased from Strem. (R)-Propylene oxide ((R)-6), (S)-1,2-epoxyhexane ((S)-10), (R)-benzyl glycidyl ether ((R)-20), 10,11-epoxyundecan-1-ol (22), 4,5-epoxypentyl butyrate (24), 5,6-epoxyhexanenitrile (26), N,N-dimethyl-10,11-undecylamide (28), trans-3,4-epoxyhexane (44), trans-2,3-epoxyoctane (46), NaCo(CO)$_4$, [(salph)Al(THF)$_2$]$^+$[Co(CO)$_4$]$^-$ (2), [(OEP)Cr(THF)$_2$]$^+$[Co(CO)$_4$]$^-$ (3), and [PPh$_4$]$^+$[Co(CO)$_4$]$^-$, were synthesized as previously reported in the literature. All other materials were commercially available and used as received.

General Considerations

All manipulations of air- and/or water-sensitive compounds were carried out under dry nitrogen using a Braun Unilab drybox or standard Schlenk line techniques. NMR spectra were recorded on a Varian Mercury spectrometer ($^1$H NMR, 300 MHz; $^{13}$C NMR, 75 MHz) and referenced versus residual non-deuterated or monoprotonated solvent shifts. Standard IR spectra were collected on a Mattson RS-10500 Research Series FTIR. In situ IR data were collected using a 100-mL Parr stainless steel high-pressure reactor modified for use with a Mettler-Toledo ReactIR 4000 Reaction Analysis System fitted with a Sentinel™ DiComp™ High Pressure Probe, and analyzed with ReactIR software version 2.21. Enantiomeric excesses were measured using either an HP 6890 Series GC equipped with an Astec α-cyclodex column, TFA chiral capillary column (250 μm×60 m), or using chiral HPLC (Waters 515 HPLC pump, Waters 2410 Refractive Index Detector, semi-prep Regis Pirkle (S,S) Whelk-O 1 column (25 cm×10 mm)). High-resolution mass spectra were obtained using electron impact conditions on a 70-VSE mass spectrometer by the Mass Spectrometry Laboratory, School of Chemical Sciences, University of Illinois. X-ray crystallographic data were collected using a Bruker X8 APEX II (Mo K$_α$, λ=0.71073 Å) at 173(2) K, and frames were integrated with the Bruker SAINT+ Program. Optimization of catalyst loading was performed in custom designed and built six-well, stainless steel, high pressure reactors, which accommodated six 4- or 8-mL glass vials. All high-pressure reactors were dried under vacuum at 90° C. prior to use.

General Procedure for the Small-Scale Carbonylation of Epoxides

A six-well, stainless steel, high pressure reactor was loaded with six 4-mL glass vials and magnetic stir bars. In a nitrogen drybox, an appropriate amount of catalyst was weighed into each vial, then solvent was added to each, with no effort made to dissolve the catalyst. Epoxide was weighed into the vials and the catalyst became soluble in the reaction mixture. Each vial was cooled in the drybox freezer at −37° C. for at least 5 min to limit ketone formation, then all were placed in the reactor. The reactor was sealed and removed from the drybox, immediately pressured with CO, stirred, and heated to the appropriate temperature. After the indicated time, the reactor was placed on dry ice, cooled to <0° C., then slowly vented. Crude reaction mixture from each vial was analyzed by $^1$H NMR spectroscopy in CDCl$_3$ to determine anhydride yields.

General Procedure for the Large-Scale Carbonylation of Epoxides

In a nitrogen drybox, a 100-mL Parr high pressure reactor was charged with the appropriate amount of catalyst and solvent, then removed from the drybox. The reactor was first pressured with 200 psi CO and stirred for 10 min, then vented down to 20 psi without stirring. The epoxide was injected via gastight syringe into the CO-filled reactor through a septum at room temperature. (This procedure of pre-saturating the solution with CO eliminated ketone formation.) The reactor was then immediately pressured to the reaction CO pressure, followed by rapid stirring and heating to the reaction temperature. After the appropriate time, the reactor was placed on dry ice, cooled to <0° C., and slowly vented.

General Procedures for Anhydride Purification

In certain embodiments, anhydrides were purified from the crude reaction mixture. Anhydrides were obtained by rotary evaporation followed by bulb-to-bulb vacuum distillation (9, 11, 15, 37, 45, 47) or sublimation (5, 7, 39, 41, 43) of the crude reaction mixture. For higher boiling anhydrides, solvent and any volatile ketones were removed from the crude reaction mixture in vacuo. The catalyst residue was then removed from the resulting oil by elution through a 2" plug of silica gel (with 1:2 EtOAc:hexanes for 13, 17, 19, 21, 23, 27, 29, 31, 33, 35, and with 4:1 EtOAc:hexanes for 25). Subsequent concentration by rotary evaporation afforded the product, which could be further purified by vacuum distillation or recrystallization from cold ether/hexane, as appropriate. Anhydrides were stable enough to be isolated and characterized, but reacted slowly with moisture to give the corresponding diacids.

Example 12

The following example describes synthetic procedures for certain catalysts used in the preceding examples.

Synthesis of $[Cl(TPP)Al(THF)_2]^+[Co(CO)_4]^-$, (1c)

This and related catalysts may be commercially available from Sigma-Aldrich. According to the method of Adler meso-tetra(4-chlorophenyl)-21H,23H-porphyrin ($ClTPPH_2$) was easily synthesized from pyrrole and 4-chlorobenzaldehyde, and dried under vacuum overnight (Adler et al., *J. Org. Chem.* 1967, 32, 476). All subsequent manipulations were performed using strict air-free techniques, and all reagents and solvents were dried and degassed prior to use. Using a modified literature procedure (Konishi et al., *J. Org. Chem.* 1990, 55, 816-820), $ClTPPH_2$ (3.44 g, 4.57 mmol) was placed in a Schlenk tube equipped with a magnetic stir-bar in a drybox. Upon removal to the bench top, the dark purple ligand was dissolved in 250 mL of $CH_2Cl_2$ to form a very dark red solution. Diethyl aluminum chloride (5.0 mL, 5.0 mmol, 1.0 M in heptane, 1.1 equiv) was added via syringe through a septum under flow of $N_2$. Ethane evolved from the reaction and was vented. The reaction was stirred at room temperature for 3 h, then solvent was removed in vacuo. The residual red-purple solid was dried under vacuum overnight and identified by comparison of its $^1$H NMR spectrum ($CDCl_3$, 300 MHz, δ): 9.10 (s, 8H), 8.13 (broad d, 8H), 7.76 (m, 8H), to that of free ligand: ($CDCl_3$, 300 MHz, δ): 8.92 (s, 8H), 7.88 (d, 8H, $^3J$=8.2 Hz), 7.49 (d, 8H, $^3J$=8.2 Hz), 2.19 (s, 2H, NH). Having reacted quantitatively, it was used without further purification. The Schlenk tube was brought into a drybox where $NaCo(CO)_4$ (887 mg, 4.57 mmol) was added. Upon removal to the Schlenk line, the solids were dissolved in 200 mL THF and stirred overnight at room temperature. The very dark, red-purple solution was concentrated to 100 mL in vacuo, and NaCl was allowed to precipitate. The solution was then filtered and layered with 200 mL hexanes. Slow diffusion over the course of a few days afforded large, purple, x-ray quality crystals that were stable under $N_2$ for over a year. (Intentional mixing of the layers results in rapid precipitation of the complex as a crystalline powder with comparable catalytic activity and selectivity). The crystals were filtered, washed with hexanes, and dried in vacuo (4.33 g, 87% yield). $^1$H NMR (300 MHz, THF-$d_8$, δ): 9.23 (s, 8H), 8.21 (m, 8H), 7.88 (m, 8H), 3.62 (m, 8H), 1.78 (m, 8H); IR (Nujol, NaCl) $v_{C=O}$=1875 cm$^{-1}$. Crystal data: monoclinic, space group $P2_1/n$, a=11.9296(6) Å, b=22.6420(12) Å, c=20.4696(10) Å, α=90°, β=102.446(2)°, γ=90°, V=5399.1(5) Å$^3$; Z=4, formula weight=1092.63 for $C_{48}H_{24}AlCl_4CoN_4O_4 \cdot 2C_4H_8O$ and density (calc.)=1.344 g/mL; R=0.0593, $R_w$=0.1634 (I>2σ(I)).

Synthesis of $[Cl(TPP)Al(THF)_2]^+[BPh_4]^-$

The synthetic procedure was identical to that for 1c, except that $NaBPh_4$ was used in place of $NaCo(CO)_4$. The structure was confirmed by X-ray crystallography.

Synthesis of $[(OEP)Al(THF)_2]^+[Co(CO)_4]^-$

The synthetic procedure was identical to that for 1c, but used the commercially available octaethylporphyrin ligand. Starting from OEP ligand (175 mg, 327 μmol) the complex was synthesized as dark red crystals (195 mg, 68%). $^1$H NMR (300 MHz, $C_6D_6$, δ): 10.56 (s, 4H), 4.12 (q, 16H), 1.92 (t, 24H), -1.42 (br s, 8H), -2.64 (br s, 8H); IR (Nujol, NaCl) $v_{C=O}$=1885 cm$^{-1}$. Structure was confirmed by X-ray crystallography, and is isostructural with $[(OEP)Cr(THF)_2]^+[Co(CO)_4]^-$.

Synthesis of $[(MeTPP)Al(THF)_2]^+[Co(CO)_4]^-$

The synthetic procedure was identical to that for 1c, but employed 4-methylbenzaldehyde in porphyrin ligand synthesis. From meso-tetra(4-methylphenyl)porphyrin (671 mg, 1.00 mmol) the complex was isolated as dark purple crystalline solid (680 mg, 67%). $^1$H NMR (300 MHz, $C_6D_6$, δ): 9.19 (s, 8H), 8.15 (m, 8H), 7.40 (m, 8H), 2.39 (s, 12H); IR (Nujol, NaCl) $v_{C=O}$=1880 cm$^{-1}$.

Synthesis of $[(TPP)Al(THF)_2]^+[Co(CO)_4]^-$

The synthetic procedure was identical to that for 1c, but employed benzaldehyde in porphyrin ligand synthesis. From tetraphenylporphyrin (1.45 g, 2.37 mmol) the complex was isolated as dark purple crystalline plates (2.16 g, 95%). $^1$H NMR (300 MHz, $C_6D_6$, δ): 9.08 (s, 8H), 8.17 (m, 8H), 7.52 (m, 12H), 3.38 (br s, 8H), 1.18 (br s, 8H); IR (Nujol, NaCl) $v_{C=O}$=1875 cm$^{-1}$.

Synthesis of $[(FTPP)Al(THF)_2]^+[Co(CO)_4]^-$

The synthetic procedure was identical to that for 1c, but employed 4-fluorobenzaldehyde in porphyrin ligand synthesis. From meso-tetra(4-fluorophenyl)porphyrin (410 mg, 0.597 mmol) the complex was isolated as dark purple crystals (340 mg, 66%). $^1$H NMR (300 MHz, THF-$d_8$, δ): 9.21 (s, 8H), 8.21 (m, 8H), 7.42 (m, 8H), 3.58 (m, 8H), 1.74 (m, 8H); IR (Nujol, NaC) $v_{C=O}$=1875 cm$^{-1}$.

Synthesis of $[(CF_3TPP)Al(THF)_2]^+[Co(CO)_4]^-$

The synthetic procedure was identical to that for 1c, but employed 4-trimethylfluorobenzaldehyde in porphyrin ligand synthesis. From meso-tetra(4-trifluoromethylphenyl)porphyrin (242 mg, 0.273 mmol) the complex was isolated as dark purple crystalline solid (258 mg, 81%). IR (Nujol, NaCl) $v_{C=O}$=1876 cm$^{-1}$.

Synthesis of Various Catalysts

[Cp$_2$Ti(THF)$_2$]$^+$[Co(CO)$_4$]$^-$ was synthesized as described in Mahadevan et al., *Angew. Chem. Int. Ed.* 2002, 41, 2781-2784.

[(salph)Al(THF)$_2$]$^+$[Co(CO)$_4$]$^-$, (2a) was synthesized as described in Getzler et al., *J. Am. Chem. Soc.* 2002, 124, 1174-1175.

[(salph)Cr(THF)$_2$]$^+$[Co(CO)$_4$]$^-$ was synthesized as described in Kramer et al., *Org. Lett.* 2006, 8, 3709-3712.

[(TPP)Cr(THF)$_2$]$^+$[Co(CO)$_4$]$^-$ was synthesized as described in Schmidt et al., *Org. Lett.* 2004, 6, 373-376.

[(OEP)Cr(THF)$_2$]$^+$[Co(CO)$_4$]$^-$, (1o), was synthesized as described in Schmidt et al., *J. Am. Chem. Soc.* 2005, 127, 11426-11435.

OTHER EMBODIMENTS

Other embodiments of the invention will be apparent to those skilled in the art from a consideration of the specification or practice of the invention disclosed herein. It is intended that the specification and Examples be considered as exemplary only, with the true scope of the invention being indicated by the following claims. The contents of any reference that is referred to herein are hereby incorporated by reference in their entirety.

What is claimed is:

1. A process for the double carbonylation of an epoxide to succinic anhydride in a reaction which comprises reacting an epoxide, where the epoxide is ethylene oxide, with carbon monoxide in a solvent in the presence of a catalytically effective amount of a catalyst, where the catalyst comprises a Lewis acid in combination with a transition metal carbonyl complex, where the Lewis acid is of the following formula:

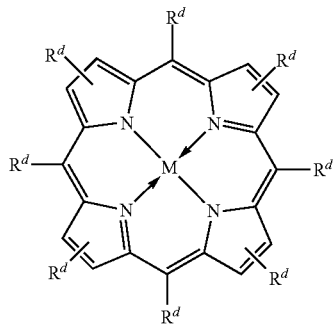

where:

M is aluminum;

R$^d$ at each occurrence is independently selected from the group consisting of: —H; C$_1$-C$_{12}$ alkyl; C$_2$-C$_{12}$ alkenyl; C$_2$-C$_{12}$ alkynyl; halogen; —OR$^{10}$; —OC(O)R$^{13}$; —OC(O)OR$^{13}$; —OC(O)NR$^{11}$R$^{12}$; —CN; —CNO; —C(O)R$^{13}$; —C(R$^{13}$)$_z$H$_{(3-z)}$; —C(O)OR$^{13}$; —C(O)NR$^{11}$R$^{12}$; —NR$^{11}$R$^{12}$; —NR$^{11}$C(O)R$^{10}$; —NR$^{11}$C(O)OR$^{13}$; —NR$^{11}$SO$_2$R$^{13}$; —NCO; —N$_3$; —NO$_2$; —S(O)$_x$R$^{13}$; —SO$_2$NR$^{11}$R$^{12}$; —C(R$^{13}$)$_z$H$_{(3-z)}$; —(CH$_2$)$_k$R$^{14}$; —(CH$_2$)$_k$-Z-R$^{16}$—; and —(CH$_2$)$_k$-Z-(CH$_2$)$_m$-R$^{14}$, and R$^{10}$ at each occurrence is independently selected from the group consisting of: —C(R$^{13}$)$_z$H$_{(3-z)}$; C$_1$ to C$_{12}$ alkyl; C$_2$ to C$_{12}$ alkenyl; C$_2$ to C$_{12}$ alkynyl; up to a C$_{12}$ carbocycle; —S(O)$_2$R$^{13}$; —Si(R$^{15}$)$_3$; —H; and a hydroxyl protecting group, R$^{11}$ and R$^{12}$ at each occurrence are independently selected from the group consisting of: —H; C$_1$ to C$_{12}$ alkyl; C$_2$ to C$_{12}$ alkenyl; C$_2$ to C$_{12}$ alkynyl; and —C(R$^{13}$)$_z$H$_{(3-z)}$;

where R$^{11}$ and R$^{12}$; when both present, can optionally be taken together with the atom to which they are attached to form a 3- to 10-membered ring, R$^{13}$ at each occurrence is independently selected from the group consisting of: —H; C$_1$ to C$_{12}$ alkyl; C$_2$ to C$_{12}$ alkenyl; C$_2$ to C$_{12}$ alkynyl; and up to a C$_{12}$ carbocycle, R$^{14}$ at each occurrence is independently selected from the group consisting of: halogen; —OR$^{10}$; —OC(O)R$^{13}$; —OC(O)OR$^{13}$; —OC(O)NR$^{11}$R$^{12}$; —CN; —CNO; —C(R$^{13}$)$_z$H$_{(3-z)}$; —C(O)R$^{13}$; —C(O)OR$^{13}$; —C(O)NR$^{11}$R$^{12}$; —NR$^{11}$C(O)R$^{13}$; —NR$^{11}$C(O)OR$^{10}$; —NR$^{11}$SO$_2$R$^{13}$; —NCO; —N$_3$; —NO$_2$; —S(O)$_x$R$^{13}$; —SO$_2$NR$^{11}$R$^{12}$; and up to a C$_{12}$ carbocycle, R$^{15}$ at each occurrence is independently selected from the group consisting of: C$_1$ to C$_6$ alkyl; C$_2$ to C$_6$ alkenyl; C$_2$ to C$_6$ alkynyl; and up to a C$_{12}$ carbocycle, R$^{16}$ at each occurrence is independently selected from the group consisting of: C$_1$ to C$_{12}$ alkyl; C$_2$ to C$_{12}$ alkenyl; C$_2$ to C$_{12}$ alkynyl; up to a C$_{12}$ carbocycle; and —C(R$^{13}$)$_z$H$_{(3-z)}$, Z is a divalent linker selected from the group consisting of:

—(CH=CH)$_a$—; —(CH≡CH)$_a$—; —C(O)—; —C(=NOR$^{11}$)—; —C(=NNR$^{11}$R$^{12}$)—; —O—; —N(R$^{11}$)—; —N(C(O)R$^{13}$)—; and —S(O)$_x$—, a is 1, 2, 3, or 4, k is an integer from 1 to 8 inclusive, m is an integer from 1 to 8 inclusive, x is 0, 1, or 2, z is 1, 2, or 3; and where the solvent includes a Lewis base and the crude yield of succinic anhydride is at least 10 percent.

2. The process of claim 1, where R$^d$ at each occurrence is independently selected from the group consisting of: —H and C$_1$-C$_{12}$ alkyl.

3. The process of claim 1, where the Lewis acid includes one or more neutral coordinating ligands.

4. The process of claim 1, where the Lewis acid includes one or more tetrahydrofuran ligands.

5. The process of claim 1, where the transition metal carbonyl complex is a monoanionic carbonyl complex of a metal from groups 5, 7 or 9.

6. The process of claim 5, where the transition metal carbonyl complex contains cobalt, manganese or rhodium.

7. The process of claim 6, where the transition metal carbonyl complex contains cobalt.

8. The process of claim 6, where the catalyst includes a transition metal carbonyl complex of formula [Co(CO)$_4$]$^-$.

9. The process of claim 1, where the Lewis acid is cationic and the transition metal carbonyl complex is anionic.

10. The process of claim 1, where the catalyst comprises a complex of formula 1a, 1b, 1c, 1d, 1e or 1f:

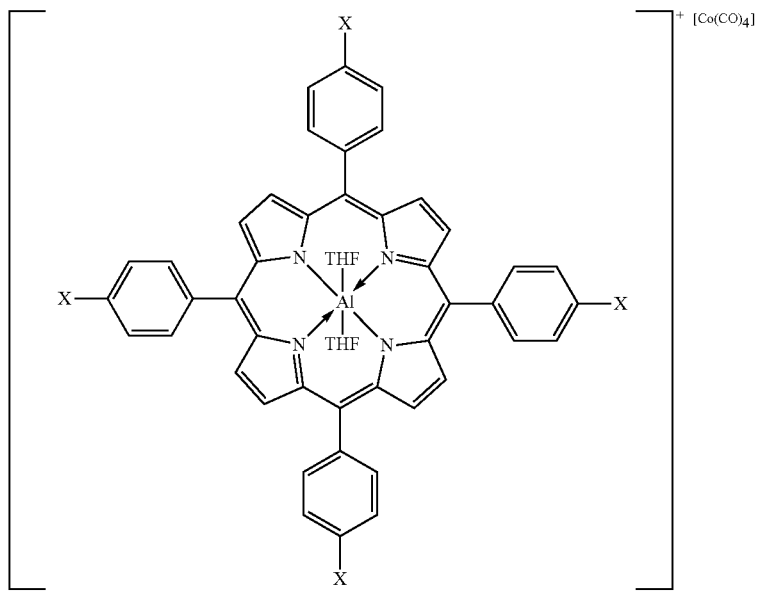

1a X = H
1b X = CH₃
1c X = Cl
1d X = F
1e X = CF₃
1f X = OCH₃

11. The process of claim 10, where the catalyst comprises a complex of formula 1c.

12. The process of claim 1, where the catalyst comprises a complex of formula 1g:

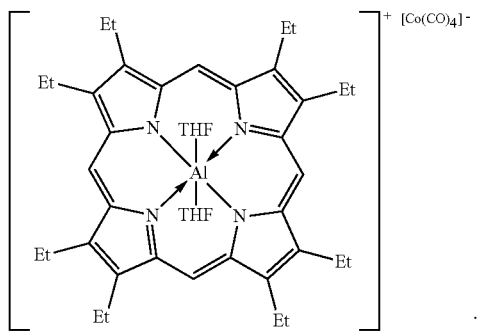

13. The process of claim 1, where the catalyst comprises a complex of formula 1a:

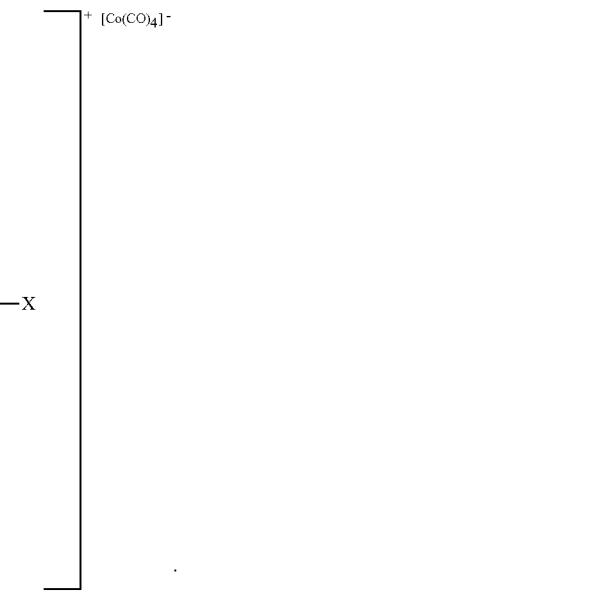

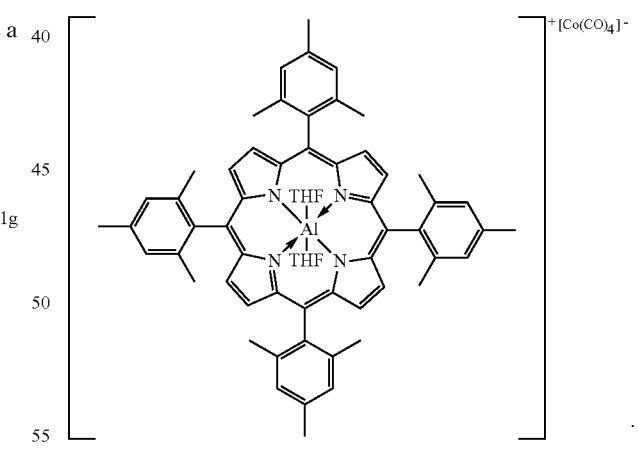

14. The process of claim 1, where the reaction is performed in a vessel and the catalyst was formed in situ by adding the Lewis acid and the transition metal carbonyl complex to the vessel.

15. The process of claim 1, where the solvent includes a Lewis base with the same polarity as 1,4-dioxane.

16. The process of claim 1, where the solvent includes a Lewis base with lower electron donicity than tetrahydrofuran.

17. The process of claim 1, where the solvent includes a Lewis base with the same electron donicity as 1,4-dioxane.

18. The process of claim 1, where the solvent includes 1,4-dioxane, tetrahydrofuran, tetrahydropyran, dimethoxyethane, glyme, diethyl ether, t-butyl methyl ether, 2,5-dimethyl tetrahydrofuran, ethyl acetate, propyl acetate, butyl acetate, acetone, 2-butanone, cyclohexanone, toluene, acetonitrile, difluorobenzene, or a combination thereof.

19. The process of claim 1, where the solvent includes 1,4-dioxane, toluene, dimethoxyethane, or a combination thereof.

20. The process of claim 1, where the solvent includes 1,4-dioxane.

21. The process of claim 1, where the solvent includes a mixture of two or more solvents.

22. The process of claim 1, where the solvent includes a mixture of 1,4-dioxane and toluene.

23. The process of claim 1, where the solvent and epoxide are the same.

24. The process of claim 1, where the reaction is conducted under a carbon monoxide pressure from about 40 psi to about 2500 psi.

25. The process of claim 1, where the crude yield of succinic anhydride is at least 80%.

26. The process of claim 1, where the crude yield of succinic anhydride is at least 90%.

27. The process of claim 1, where the crude yield of succinic anhydride is at least 95%.

* * * * *